US012691440B2

(12) United States Patent
Miyake et al.

(10) Patent No.: US 12,691,440 B2
(45) Date of Patent: Jul. 28, 2026

(54) PHOTOREDOX CATALYSTS AND METHODS OF USING SUCH CATALYSTS

(71) Applicants: Colorado State University Research Foundation, Fort Collins, CO (US); New Iridium Inc., Superior, CO (US)

(72) Inventors: Garret M. Miyake, Fort Collins, CO (US); Justin P. Cole, Fort Collins, CO (US); Ryan M. Pearson, Fort Collins, CO (US); Chern-Hooi Lim, Superior, CO (US); Max Kudisch, Fort Collins, CO (US); Dian-Feng Chen, Fort Collins, CO (US)

(73) Assignees: Colorado State University Research Foundation, For Collins, CO (US); New Iridium, Inc., Superior, CO (US)

( * ) Notice: Subject to any disclaimer, the term of this patent is extended or adjusted under 35 U.S.C. 154(b) by 903 days.

(21) Appl. No.: 17/790,027

(22) PCT Filed: Jan. 11, 2021

(86) PCT No.: PCT/US2021/012960
§ 371 (c)(1),
(2) Date: Jun. 29, 2022

(87) PCT Pub. No.: WO2021/142444
PCT Pub. Date: Jul. 15, 2021

(65) Prior Publication Data

US 2023/0090784 A1 Mar. 23, 2023

Related U.S. Application Data

(60) Provisional application No. 62/959,008, filed on Jan. 9, 2020.

(51) Int. Cl.
*C08F 2/48* (2006.01)
*B01J 31/00* (2006.01)
(Continued)

(52) U.S. Cl.
CPC ......... *B01J 31/0247* (2013.01); *B01J 31/006* (2013.01); *B01J 35/39* (2024.01); *C07D 209/62* (2013.01)

(58) Field of Classification Search
None
See application file for complete search history.

(56) References Cited

PUBLICATIONS

Keshri et al. Chemistry A Europe Journal, 2018, 24, 1821-1832). (Year: 2018).*

(Continued)

*Primary Examiner* — Yun Qian
(74) *Attorney, Agent, or Firm* — Berg Hill Greenleaf Ruscitti LLP

(57) ABSTRACT

The disclosure relates to photoredox catalysts (PC) and methods for the Birch reductions of aromatic substrates, such as benzene, benzeneoid, and heteroaromatic compounds, using light as the driving force. Certain aspects of the disclosure encompass methods for reduction of aromatic substrates. The method comprises contacting an aromatic substrate with a sacrificial electron donor in the presence of a photoredox catalyst in a solvent, thereby forming a reaction mixture; exposing the reaction mixture to visible or UV light under reaction condition sufficient to reduce the aromatic substrate compound.

7 Claims, 7 Drawing Sheets

Reduction of Aryl Ethers

A PC (0.25 mol% x 6), $NMe_4OH$ (5 eq x 3), MeOH/$^t$AmylOH, 405 nm, rt, 168 h

Reductive Deoxygenation and Birch Reduction

B PC (0.25 mol% x 3), $NMe_4OH$ (5 eq x 3), MeOH/$^t$AmylOH, 405 nm, rt, 96 h

(51) Int. Cl.

*B01J 31/02* (2006.01)
*B01J 35/39* (2024.01)
*C07D 209/62* (2006.01)

(56) References Cited

PUBLICATIONS

Gosh I et al: "Reduction of aryl halides by consecutive visible light-induced electron transfer processes", Science, vol. 346, No. 6210, Nov. 7, 2014 (Nov. 7, 2014), pp. 725-728, XP002785221.

Verma Shruti et al: "Benzo[ghi]perylene monoimide based photosensitive lamellar Cd-doped ZnO nanohybrids", RSC Adv., vol. 4, No. 107, Jan. 1, 2014 (Jan. 1, 2014), pp. 62603-62614, XP055826161, DOI: 10.1039/C4RA13712D.

Rao K. Venkata et al: "Synthesis and Controllable Self-Assembly of a Novel Coronene Bisimide Amphiphile", Organic Letters, vol. 12, No. 11, Jun. 4, 2010 (Jun. 4, 2010), pp. 2656-2659, XP055826153, ISSN: 1523-7060, DOI: 10.1021/ol100864e.

Alibert-Fouet Sonia et al: "Liquid-Crystalline and Electron-Deficient Coronene Oligocarboxylic Esters and Imides by Twofold Benzogenic Diels-Alder Reactions on Perylenes", Chemistry—A European Journal, vol. 13, No. 6, Nov. 17, 2006 (Nov. 17, 2006), pp. 1746-1753, XP055825719, ISSN: 0947-6539, DOI: 10.1002/chem.200601416.

Masahide Yasuda et al: "Photochemical reactions of aromatic compounds. 35. Photo-Birch reduction of arenes with sodium borohydride in the presence of dicyanobenzene", The Journal of Organic Chemistry, vol. 46, No. 4, Feb. 1, 1981 (Feb. 1, 1981), pp. 788-792, XP055493590, ISSN: 0022-3263, DOI: 10.1021/jo00317a028.

Saha Sourav: "Anion-Induced Electron Transfer", Accounts of Chemical Research, vol. 51, No. 9, Sep. 7, 2018 (Sep. 7, 2018), pp. 2225-2236, XP055829273, ISSN: 0001-4842, DOI: 10.1021 /acs.accounts.8b00197.

Kurpanik Aneta et al: "Diels-Alder Cycloaddition to the Bay Region of Perylene and Its Derivatives as an Attractive Strategy for PAH Core Expansion: Theoretical and Practical Aspects", Molecules, vol. 25, No. 22, 5373, Nov. 1, 2020 (Nov. 1, 2020), pp. 1-50, XP055825290, ISSN: 1433-1373, DOI: 10.3390/molecules25225373.

Cole Justin P. et al: "Organocatalyzed Birch Reduction Driven by Visible Light", Journal of the American Chemical Society, vol. 142, No. 31, Jul. 14, 2020 (Jul. 14, 2020), pp. 13573-13581, XP55825701, ISSN: 0002-7863, DOI: 10.1021 /jacs.0c05899.

International Search Report in international application No. PCT/US2021/012960 mailed Nov. 8, 2021, 3 pages.

Written Opinion/International Preliminary Examination Report in international application No. PCT/US2021/012960 mailed Nov. 8, 2021, 8 pages.

* cited by examiner

Reduction of Aryl Ethers

A PC (0.25 mol% x 6), $NMe_4OH$ (5 eq x 3), MeOH/$^t$AmylOH, 405 nm, rt, 168 h

Reductive Deoxygenation and Birch Reduction

B PC (0.25 mol% x 3), $NMe_4OH$ (5 eq x 3), MeOH/$^t$AmylOH, 405 nm, rt, 96 h

Selective Reduction
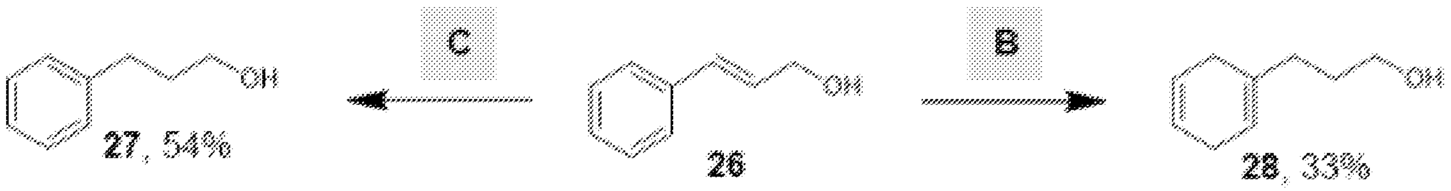
27, 54%
26
28, 33%
C PC (0.25 mol%), $NMe_4OH$ (5 eq), MeOH/$^t$AmylOH, 405 nm, rt, 24 h
FIG. 1C
Reductive Ring-Opening and Birch Reduction
30, 73%
FIG. 1D
29
FIG. 1E
31, 40%
D PC (0.25 mol% x 2), $NMe_4OH$ (10 eq), MeOH/$^t$AmylOH, 405 nm, rt, 72 h
E PC (0.25 mol% x 5), $NMe_4OH$ (15 eq), MeOH/$^t$AmylOH, 405 nm, rt, 144 h FIG. 4A
A
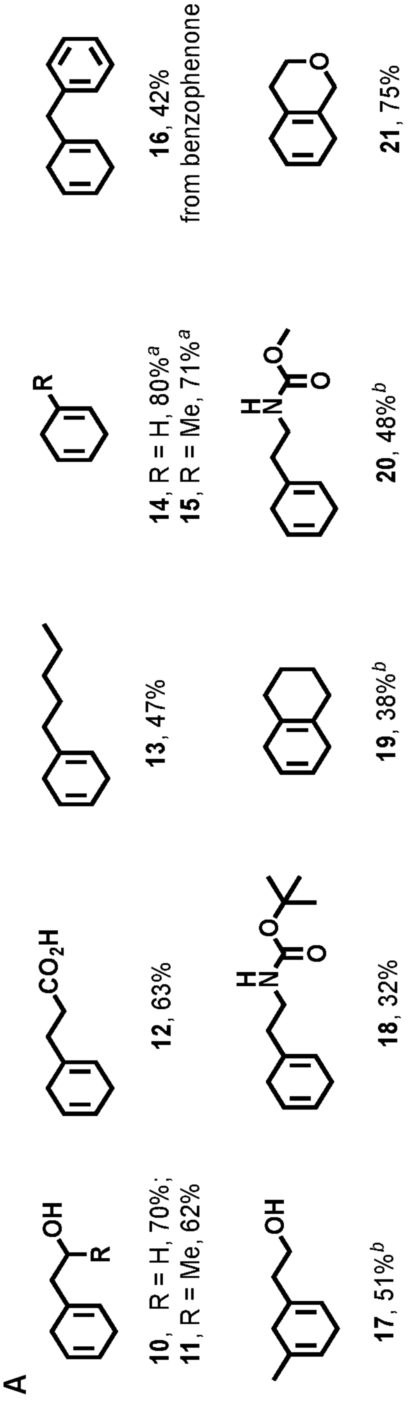
10, R = H, 70%;
11, R = Me, 62%
12, 63%
13, 47%
14, R = H, 80%[a]
15, R = Me, 71%[a]
16, 42%
from benzophenone
17, 51%[b]
18, 32%
19, 38%[b]
20, 48%[b]
21, 75%
B
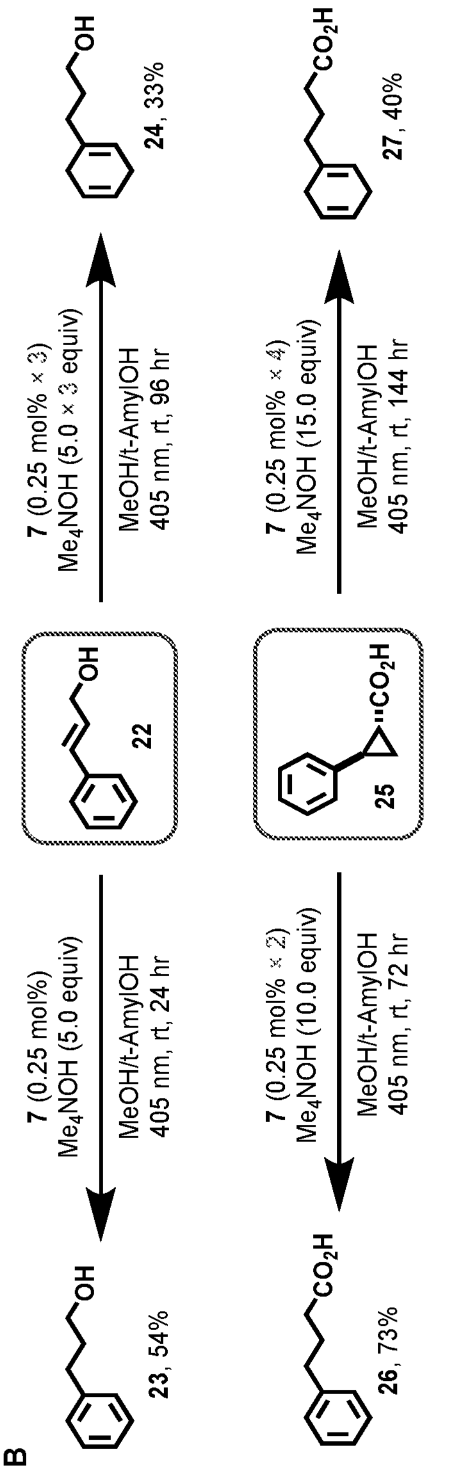
23, 54%
22
24, 33%
26, 73%
25
27, 40%
FIG. 4B

PHOTOREDOX CATALYSTS AND METHODS OF USING SUCH CATALYSTS

CROSS-REFERENCE TO RELATED APPLICATION

This application is a national stage application under 35 U.S.C. 371 of PCT Application No. PCT/US2021/012960 having an international filing date of Jan. 11, 2021, which designated the United States, which PCT application claimed the benefit of U.S. Application Ser. No. 62/959,008, filed Jan. 9, 2020, both of which are incorporated by reference in their entirety. #

GOVERNMENTAL RIGHTS

This invention was made with government support under R35GM119702 awarded by the National Institutes of Health. The government has certain rights in the inventions disclosed.

FIELD OF THE INVENTION

The present disclosure generally relates to photoredox catalysts and methods of using such catalysts in photoredox catalytic reactions, including the reduction of aromatic compounds via light-driven reactions using these photoredox catalysts.

BACKGROUND OF THE INVENTION

Visible-light photoredox catalysis has transformed the synthesis of small molecules and materials through the conversion of photochemical energy to chemical potentials enabling unique reactivity under mild conditions.[18-22] However, the scope of accessible chemical transformations using these catalytic platforms is fundamentally confined by the energetics of a visible photon. For example, a 400 nm photon provides 3.1 eV of energy, defining the upper limit for the thermodynamic driving force for transformations using visible light. Thus, the low electron affinity of inert substrates such as benzene render it unreactive and difficult to reduce by single electron transfer, requiring a reduction potential of −3.42 V vs SCE,[22] while the high triplet energy of benzene (3.6 eV) prevents triplet energy sensitization.[23] As such, the reduction of benzene requires harsher conditions than accessible by current visible-light photoredox catalyst systems.

The Birch reduction—the prototypical example being the overall 2e−/2H+ reduction of benzene to 1,4-cyclohexadiene-represents one of the most demanding reductions in organic synthesis and traditionally employs solvated electrons as the reductant, generated using lithium or sodium metal under cryogenic liquid ammonia conditions.[24,25] Several variations of Birch reductions have been developed, including ammonia free,[26] electrochemical,[27,28] and photochemical,[29] each of which has increased the safety of performing Birch reductions.

Despite these advances, the development of a mild, metal-free, visible-light-driven Birch reduction is highly desirable.

BRIEF DESCRIPTION OF FIGURES

FIG. 1A-1F illustrates exemplary selective reduction methodologies in accordance with embodiments of the disclosure. (A) Reduction of aryl ethers. (B) Reductive deoxygenation and Birch reduction. (C) Selective vinyl reduction. (D) Reductive ring opening alone and (E) in combination with Birch reduction. (F) Late stage dehalogenation.

FIG. 4A-4B. Scope of photoredox Birch reduction. (A) Birch reduction products. (B) Selective reductions. [a]Determined using $^1H$ NMR with 1,3,5-trimethoxybenzene as an internal standard. [b] 144 hr reaction time.

SUMMARY OF THE INVENTION

Figure 1A:
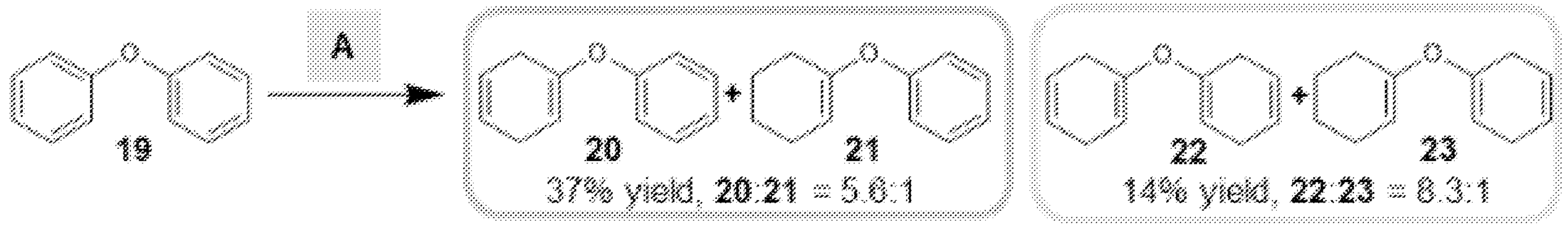

In one aspect, disclosed herein, is a photoredox catalyst comprising Formula (I) or a salt thereof:

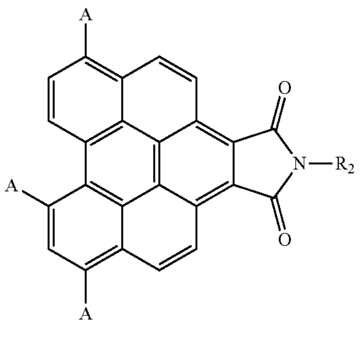

wherein:

A is selected from —H, an optionally substituted $C_1$ to $C_{16}$ alkyl, an optionally substituted aryl, or an optionally substituted heteroaryl; and $R_2$ is selected from an optionally substituted $C_1$ to $C_{16}$ alkyl, an optionally substituted aryl, or an optionally substituted heteroaryl.

In some embodiments, A may be selected from:

A = $R_1$ ;

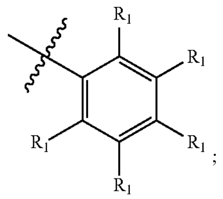

;

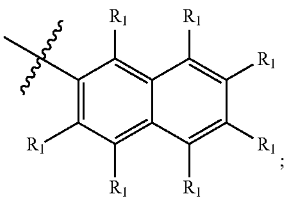

; or

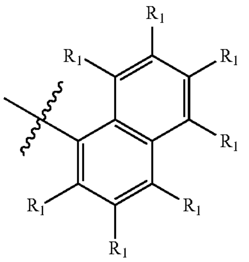

wherein:

$R_1$ is selected from —H, halogen, —CN, —$OR_3$, —C(O)$R_3$, —C(O)$OR_3$, —C(O)$NR_4R_5$, —$NO_2$, —$NR_4R_5$, —$SR_3$, —S(O)$R_3$, —$S(O)_2R_3$, $C_1$ to $C_8$ substituted alkyl, $C_1$ to $C_8$ unsubstituted alkyl, substituted aryl, unsubstituted aryl, substituted heteroaryl, or unsubstituted heteroaryl;

$R_3$ is selected from —H, —$NR_4R_5$, $C_1$ to $C_8$ substituted alkyl, or $C_1$ to $C_8$ unsubstituted alkyl, substituted aryl, unsubstituted aryl, substituted heteroaryl, or unsubstituted heteroaryl; and $R_4$ and $R_5$ are each independently selected from —H, $C_1$ to $C_8$ substituted alkyl, $C_1$ to $C_8$ unsubstituted alkyl, substituted aryl, unsubstituted aryl, substituted heteroaryl, or unsubstituted heteroaryl.

In other aspects, methods of using the photoredox catalyst of Formula (I) in photoredox catalyzed reactions are provided. The methods may be light driven selective reduction reactions comprising: contacting a substrate with a sacrificial electron donor in the presence of a photoredox catalyst, e.g., a photoredox catalyst of Formula (I), and a solvent thereby forming a reaction mixture; exposing the reaction mixture to light under reaction conditions sufficient to reduce the substrate. In certain embodiments, the selective reduction reactions include Birch reduction, reductive deoxygenation, reductive ring-opening, reductive dehalogenation, vinyl reduction, ether reduction, and combinations thereof.

In certain embodiments, the methods of the disclosure relate to methods for reducing an aromatic substrate, the methods comprising: contacting the aromatic substrate with a sacrificial electron donor in the presence of a photoredox catalyst, e.g., a photoredox catalyst of Formula (I), and a solvent thereby forming a reaction mixture; exposing the reaction mixture to light under reaction conditions sufficient to reduce the aromatic substrate. In some embodiments, the aromatic substrate may be activated or unactivated.

In another aspect, provided herein, are methods for preparing the photoredox catalyst comprising Formula (I) or a salt thereof:

Formula (I)

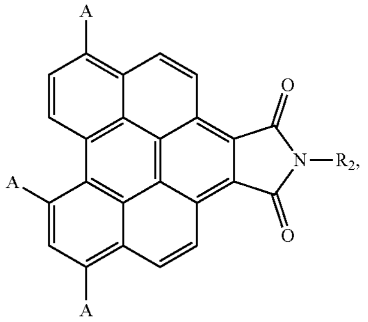

The methods comprising: (a) contacting the compound of Formula (II):

Formula (II)

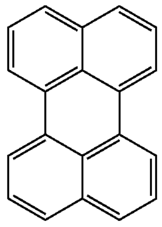

;

with maleic anhydride and p-chloroanil to form the compound comprising Formula (III):

Formula (III)

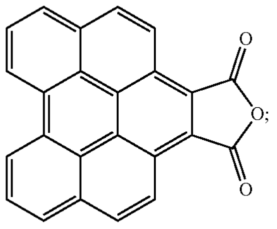

(b) contacting the compound comprising Formula (III) with an aliphatic amine to form the compound comprising Formula (IV):

Formula (IV)

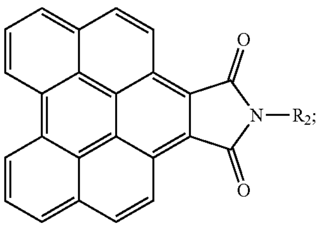

(c) contacting the compound comprising Formula (IV) with a halogenating agent to form the compound comprising Formula (V);

Formula (V)

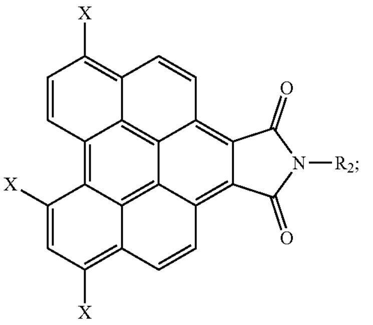

and (d) contacting the compound comprising Formula (V) with an aryl boronic acid in the presence of a catalyst to form the photoredox catalyst comprising Formula (I) or a salt thereof.

wherein:

A is selected from —H, an optionally substituted $C_1$ to $C_{16}$ alkyl, an optionally substituted aryl, or an optionally substituted heteroaryl;

$R_2$ is selected from an optionally substituted $C_1$ to $C_{16}$ alkyl, an optionally substituted aryl, or an optionally substituted heteroaryl; and X is selected from a group consisting of chloride, bromide, or iodide.

Other features and iterations of the invention are described in more detail below.

DETAILED DESCRIPTION OF THE INVENTION

In accordance with aspects of the disclosure, photoredox catalysts and related chemistry have been investigated as a complementary "green" approach to perform selective reduction reactions, including Birch reductions without the use of an alkali metal, liquid $NH_3$, or cryogenic temperatures. The photoredox catalytic reduction catalysts and methods of the disclosure can be used in a variety of chemistries, including, e.g., terpenoid synthesis, removal of protecting groups, deoxygenation of ketones, reductive dehalogentation, and reductive bond-forming reactions.

Consecutive photoinduced electron transfer (ConPET) was first reported as a way to reduce aryl-halide bonds using organic photocatalysts (PC).[3] The Ar—X reduction requires relatively high reduction potentials ($E_{red}$<−2.0 V vs. SCE) which is difficult to achieve using visible light photons. The ConPET mechanism utilizes a two-photon process, where one photon generates the PC radical anion ($PC^{•-}$) and the second photon excites the radical anion to generate the extremely reducing excited state $PC^{•-}*$.[4] In this system, the reduction potential for $PC^{•-}*$ can be calculated as the sum of the ground state reduction potential $E^0(PC/PC^{•-})$ and the energy difference of the SOMO+1 and the SOMO. The first report of ConPET utilized a perylene diimide photoredox (PDI) catalysts with a relatively mild ground state reduction potential $[E_0(PC/PC^{•-})=-0.37$ V vs. SCE]. In the case of PDI, the $PC^{•-}*$ is ~1.6 V more reducing than the $PC^{•-}$, and $PC^{•-}*$ was able to reduce the aryl-chloride bonds.

The limitation to the reducing power of ConPET is the ground state reduction potential of the photocatalyst. In accordance with aspects of the disclosure, and without intending to be limited by theory, an organic dye with a reversible reduction potential much greater than PDI $[E_0(PC/PC^{•-})>-0.37$ V vs. SCE] was chosen so as to enable a more powerful ConPET reaction. In this regard, without limitation, benzo[ghi]peryelene monoimide (BPI), and substitutions and derivatives thereof, were chosen as the dye because of its high reversible reduction potential $[E_0(PC/PC^{•-})=-1.25$ V vs. SCE].[5]

Without intending to be limited by theory, because of this high ground state reduction potential, a photoexcited BPI radical anion's excited state reduction potential $E^0(PC/PC^{•-}*)$ would be great enough to reduce an arene to an arene radical anion. In this regard, if this thermodynamically challenging photoinduced electron transfer (PET) between dye and reactant is successful, the rest of the Birch reduction would be thermodynamically downhill.[6,7]

Advantageously, these reductions are environmentally friendly, easily conducted, and can be scaled.

(I) A Photoredox Catalyst

In one aspect, a class of organic benzo[ghi]perylene imide photoredox catalysts are provided, which are particularly suited for selected reduction reaction such as Birch reductions under mild benchtop conditions and visible-light LED irradiation. In accordance with aspects of the disclosure, the photoredox catalysts provide a visible-light photoredox catalysis system that is capable of engaging arenes such as benzene that were previously out of reach due to their high triplet energies and extremely negative reduction potentials. Without intending to be limited by theory, mechanistic experiments support formation of the hydroxide adduct $[PC—OH]^-$ and its subsequent photodissociation to $PC^{•-}$, which thereafter may undergo absorption of a second photon to release a solvated electron as an active reductant.

In one embodiment, the present disclosure provides a photoredox catalyst comprising Formula (I) or a salt thereof:

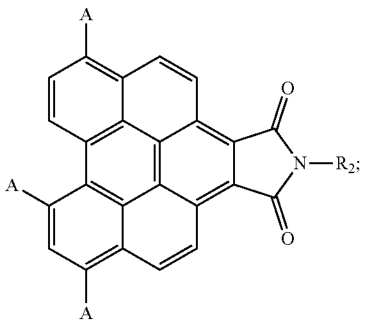

wherein:

A is selected from —H, an optionally substituted $C_1$ to $C_{16}$ alkyl, an optionally substituted aryl, or an optionally substituted heteroaryl; and $R_2$ is selected from an optionally substituted $C_1$ to $C_{16}$ alkyl, an optionally substituted aryl, or an optionally substituted heteroaryl.

In some embodiments, A may be selected from:

$A = R_1$ ;

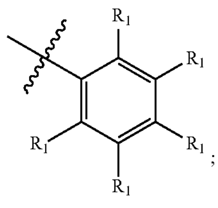

;

-continued

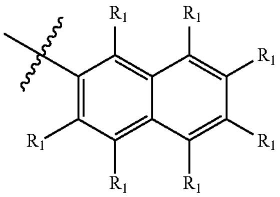

; or

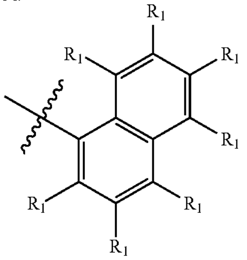

wherein:

$R_1$ is selected from —H, halogen, —CN, —$OR_3$, —C(O)$R_3$, —C(O)$OR_3$, —C(O)$NR_4R_5$, —$NO_2$, —$NR_4R_5$, —$SR_3$, —S(O)$R_3$, —$S(O)_2R_3$, $C_1$ to $C_8$ substituted alkyl, $C_1$ to $C_8$ unsubstituted alkyl, substituted aryl, unsubstituted aryl, substituted heteroaryl, or unsubstituted heteroaryl;

$R_3$ is selected from —H, —$NR_4R_5$, $C_1$ to $C_8$ substituted alkyl, or $C_1$ to $C_8$ unsubstituted alkyl, substituted aryl, unsubstituted aryl, substituted heteroaryl, or unsubstituted heteroaryl; and $R_4$ and $R_5$ are each independently selected from —H, $C_1$ to $C_8$ substituted alkyl, $C_1$ to $C_8$ unsubstituted alkyl, substituted aryl, unsubstituted aryl, substituted heteroaryl, or unsubstituted heteroaryl.

Generally, in accordance with embodiments, $R_1$ may be selected from —H, halogen, —CN, —$OR_3$, $NR_4R_5$, $C_1$ to $C_8$ substituted alkyl, $C_1$ to $C_8$ unsubstituted alkyl, substituted aryl, unsubstituted aryl, substituted heteroaryl, or unsubstituted heteroaryl. In some embodiments, $R_1$ is selected from —H, $C_1$-$C_6$ alkyl, $C_1$-$C_6$ haloalkyl, optionally substituted phenyl, —OH, —O($C_1$-$C_6$ alkyl), —$NO_2$, —CN, —C(═O)OH, —C(═O)O($C_1$-$C_6$ alkyl), —C(═O)O-phenyl, —C(═O)($C_1$-$C_6$ alkyl), —C(═O)-phenyl, —$S(O)_2NH_2$, —$S(O)_2NH$($C_1$-$C_6$ alkyl), —$S(O)_2N$($C_1$-$C_6$ alkyl)($C_1$-$C_6$ alkyl), —S($C_1$-$C_6$ alkyl), —S(O)($C_1$-$C_6$ alkyl), —$S(O)_2$($C_1$-$C_6$ alkyl), —S(phenyl), —S(O)(phenyl), and —$S(O)_2$(phenyl). In some embodiments, $R_1$ is selected from a group consisting of —H, halogen, —CN, —$OR_3$, —$NR_4R_5$, $C_1$-$C_4$ substituted alkyl, $C_1$-$C_4$ unsubstituted alkyl, substituted aryl, unsubstituted aryl, substituted heteroaryl, or unsubstituted heteroaryl. In certain embodiments, $R_1$ is selected from a group consisting of —H, fluoride, chloride, bromide, —CN, —$OR_3$, —$NR_4R_5$, methyl, ethyl, n-propyl, iso-propyl, n-butyl, sec-butyl, iso-butyl, t-butyl, —$CCl_3$, —$CF_3$, phenyl, 1-napthyl, 2-napthyl, and 1-napthyl and 2-napthyl substituted with an $R_3$ group. In specific embodiments, $R_1$ is selected from a group consisting of —H, bromide, —CN, —$OR_3$, —$NR_4R_5$, —$CF_3$, or phenyl.

In general, in accordance with embodiments, $R_2$ is selected from $C_1$ to $C_{16}$ substituted alkyl, $C_1$ to $C_{16}$ unsubstituted alkyl, substituted aryl, unsubstituted aryl, substituted heteroaryl, or unsubstituted heteroaryl. In some embodiments, $R_2$ is selected from a $C_1$ to $C_{16}$ substituted or unsubstituted alkyl. In some embodiments, $R_2$ is selected from a $C_1$ to $C_{12}$ substituted or unsubstituted alkyl. In certain embodiments, $R_2$ is selected from a $C_1$ to $C_8$ substituted or unsubstituted alkyl. In specific embodiments, $R_2$ is 2-ethylhexyl. In other embodiments, $R_2$ is selected from a substituted or unsubstituted phenyl. In other embodiments, $R_2$ is selected from a substituted or unsubstituted napthyl, e.g., 1-napthyl or 2-napthyl.

Generally, in accordance with embodiments, $R_3$ is selected from —H, —$NR_4R_5$, $C_1$ to $C_8$ substituted alkyl, or $C_1$ to $C_8$ unsubstituted alkyl, substituted aryl, unsubstituted aryl, substituted heteroaryl, or unsubstituted heteroaryl. In some embodiments, $R_3$ is selected from a —H, $C_1$ to $C_8$ substituted alkyl, or $C_1$ to $C_8$ unsubstituted alkyl. In some embodiments, $R_3$ is selected from H, $C_1$ to $C_4$ substituted alkyl, or $C_1$ to $C_4$ unsubstituted alkyl. In certain embodiments, $R_3$ is selected from H, methyl, ethyl, n-propyl, iso-propyl, n-butyl, sec-butyl, iso-butyl, or t-butyl. In specific embodiments, $R_3$ is methyl.

In general, in accordance with embodiments, $R_4$ and $R_5$ are each independently selected from —H, $C_1$ to $C_8$ substituted alkyl, $C_1$ to $C_8$ unsubstituted alkyl, substituted aryl, unsubstituted aryl, substituted heteroaryl, or unsubstituted heteroaryl. In some embodiments, $R_4$ and $R_5$ are independently selected from H, $C_1$ to $C_8$ substituted alkyl, or $C_1$ to $C_8$ unsubstituted alkyl. In some embodiments, $R_4$ and $R_5$ are independently selected from H, $C_1$ to $C_4$ substituted alkyl, or $C_1$ to $C_4$ unsubstituted alkyl. In certain embodiments, $R_4$ and $R_5$ are independently selected from H, methyl, ethyl, n-propyl, iso-propyl, n-butyl, sec-butyl, iso-butyl, or t-butyl. In specific embodiments, $R_4$ and $R_5$ are H or methyl.

In some embodiments, A may be a phenyl group, optionally substituted with one or more $R_1$ groups. By way of non-limiting example, photoredox catalysts of Formula (I) may include the following:

Formula (Ia)

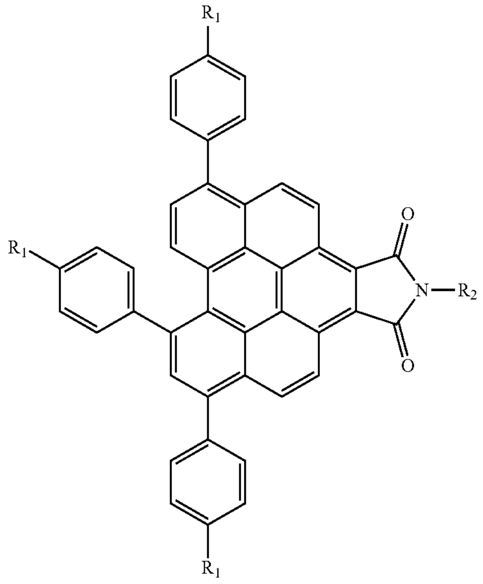

-continued
Formula (Ib)
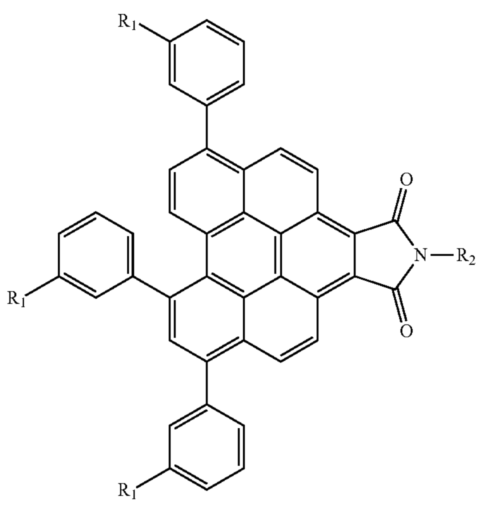
Formula (Ic)
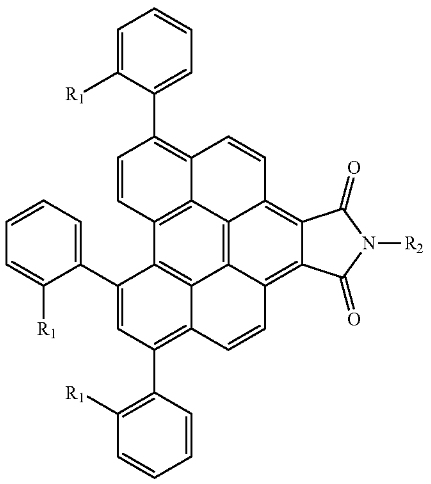
Formula (Id)
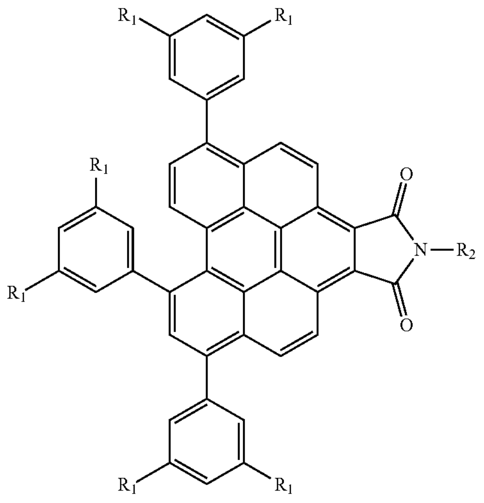
-continued
Formula (Ie)
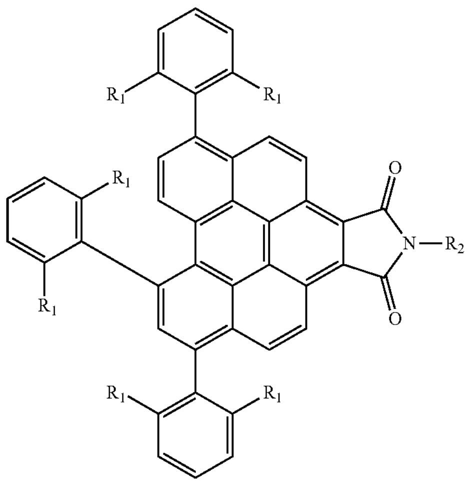
Formula (If)
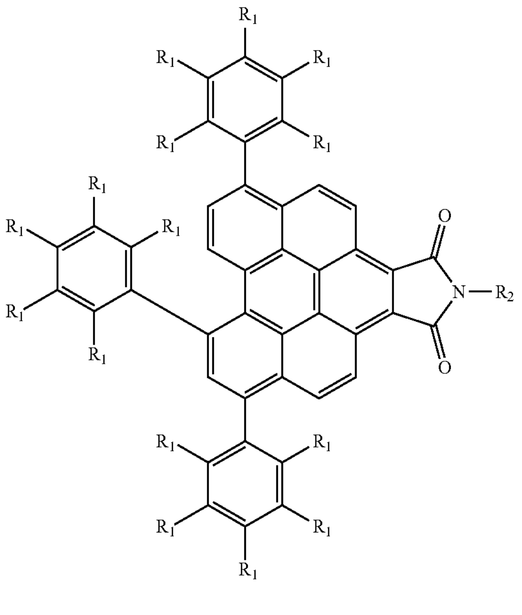
In some embodiments, $R_1$ may be independently selected from —H, or —OMe. Examples are illustrated below.

-continued
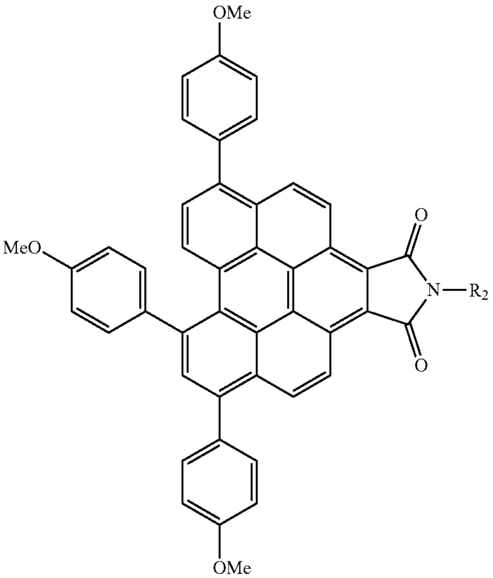
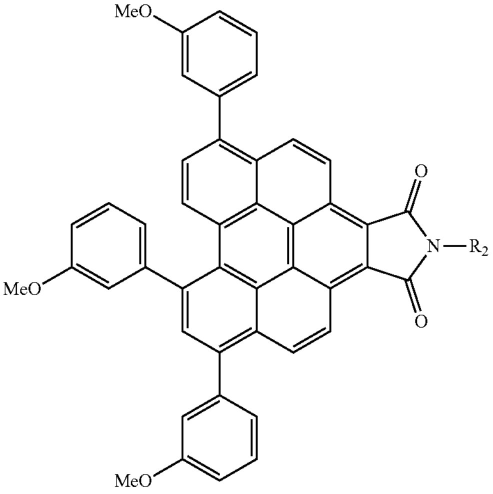
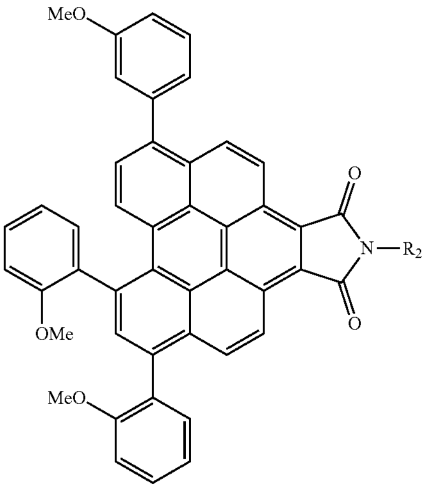
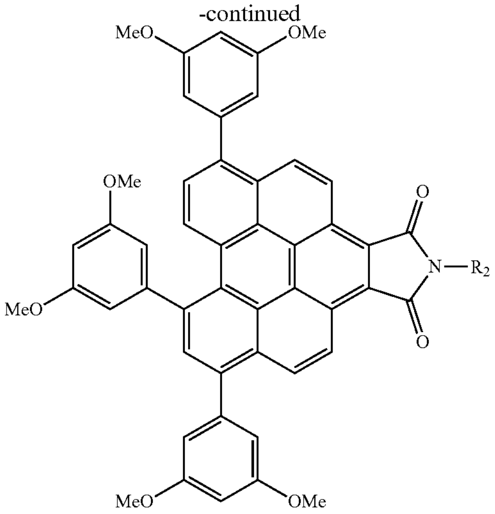
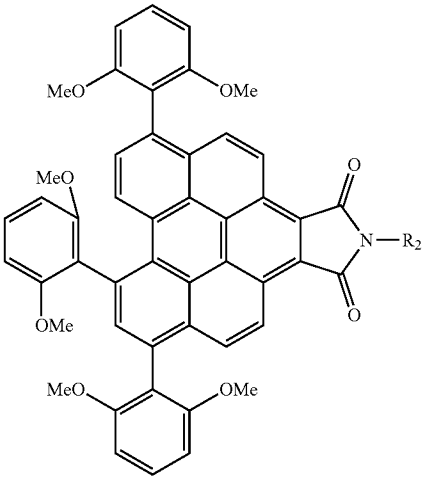
In other embodiments, A may be a napthyl group (e.g., 1-napthyl, 2-napthyl, optionally substituted with one or more $R_1$ groups). Examples are illustrated below.

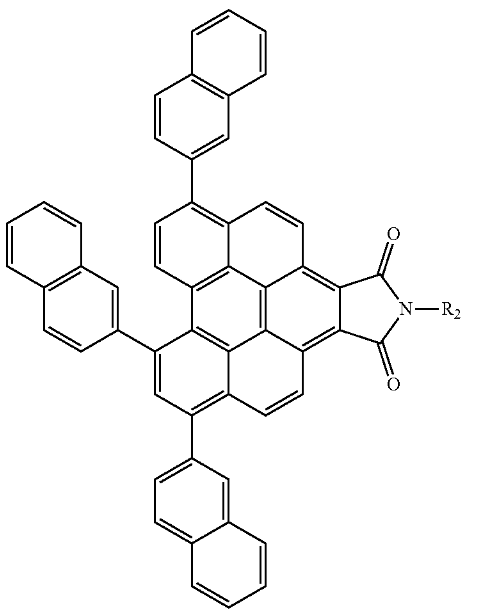

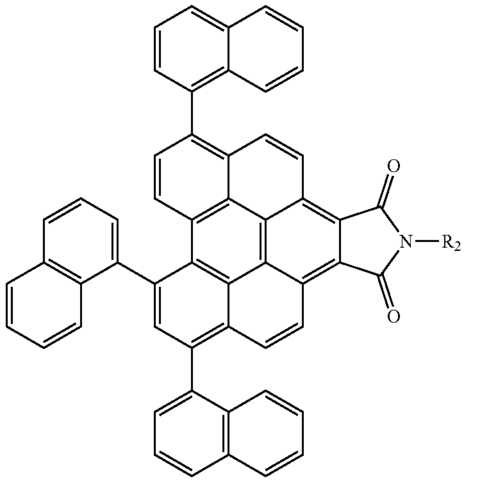

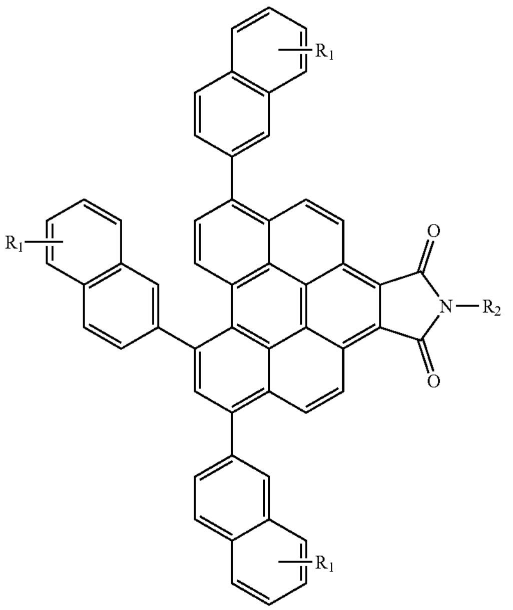

-continued

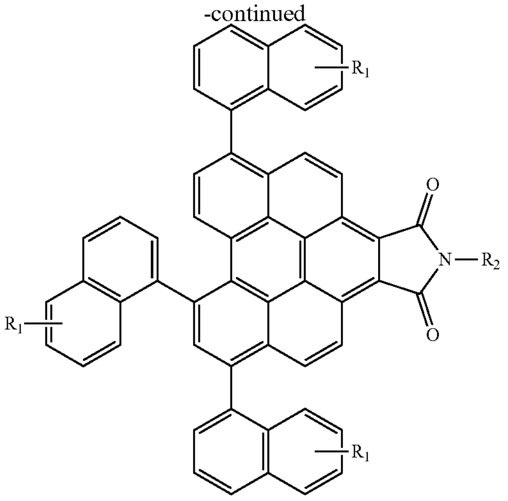

(II) Methods for Selective Reduction.

In other aspects, methods of using the photoredox catalyst of Formula (I) in photoredox catalyzed reactions are provided. The methods may be light driven selective reduction reactions comprising: contacting a substrate with a sacrificial electron donor in the presence of a photoredox catalyst, e.g., a photoredox catalyst of Formula (I), and a solvent thereby forming a reaction mixture; exposing the reaction mixture to light under reaction conditions sufficient to reduce the substrate. In certain embodiments, the selective reduction reactions include Birch reduction, reductive deoxygenation, reductive ring-opening, reductive dehalogenation, vinyl reduction, ether reduction, and combinations thereof.

By way of example, the photoredox catalysts of the disclosure may be used in selective reduction reactions. With reference to FIG. 1A-F, in accordance with certain embodiments, selective reduction of arenes containing multiple reactive unsaturated functional groups can be achieved through modulation of the reaction conditions.

In one embodiment, as shown in FIG. 1A, methods of the disclosure may provide for the reduction of aryl ethers. As illustrated, reduction of one or both phenyl rings of diphenyl ether may be observed (20 and 22), as well as the over-reduction to afford vinyl ethers 21 and 23.

Figure 1B:
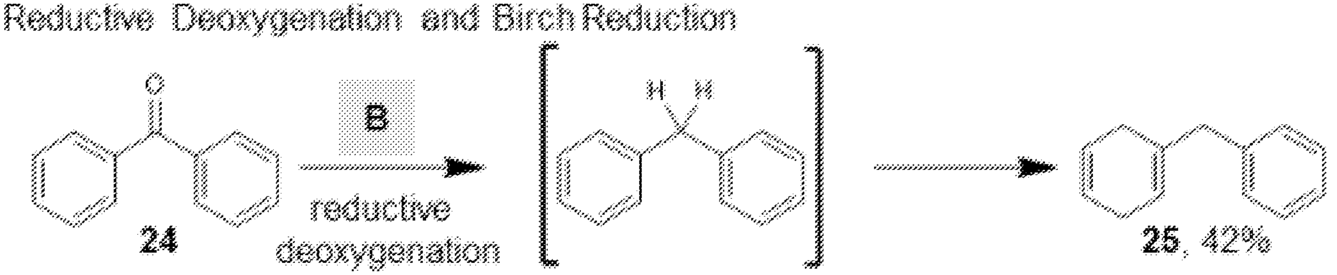

In another embodiment, as shown in FIG. 1B, methods of the disclosure may provide for the reductive deoxygenation of a carbonyl in combination with Birch reduction. As illustrated, employing optimized conditions, benzophenone may proceed through the tandem reductive deoxygenation and Birch reduction to afford 1-benzyl-1,4-cyclohexadiene 25 in 42% yield.

In another embodiment, as shown in FIG. 1C, methods of the disclosure may provide for selective reduction. As illustrated, by manipulating the equivalents of $NMe_4OH$ and reaction time, cinnamyl alcohol may be converted to either phenylpropanol 27 through alkene reduction or 28 via both alkene and aromatic reductions.

In yet another embodiment, as shown in FIG. 1C and FIG. 1D, methods of the disclosure may provide for reductive ring-opening alone or in combination with Birch reduction. As illustrated, trans-2-phenylcyclopropane-1-carboxylic acid may undergo a reductive ring-opening process to give 30 in 73% yield, while further reduction may provide 31 in 40% yield.

Figure 1F:
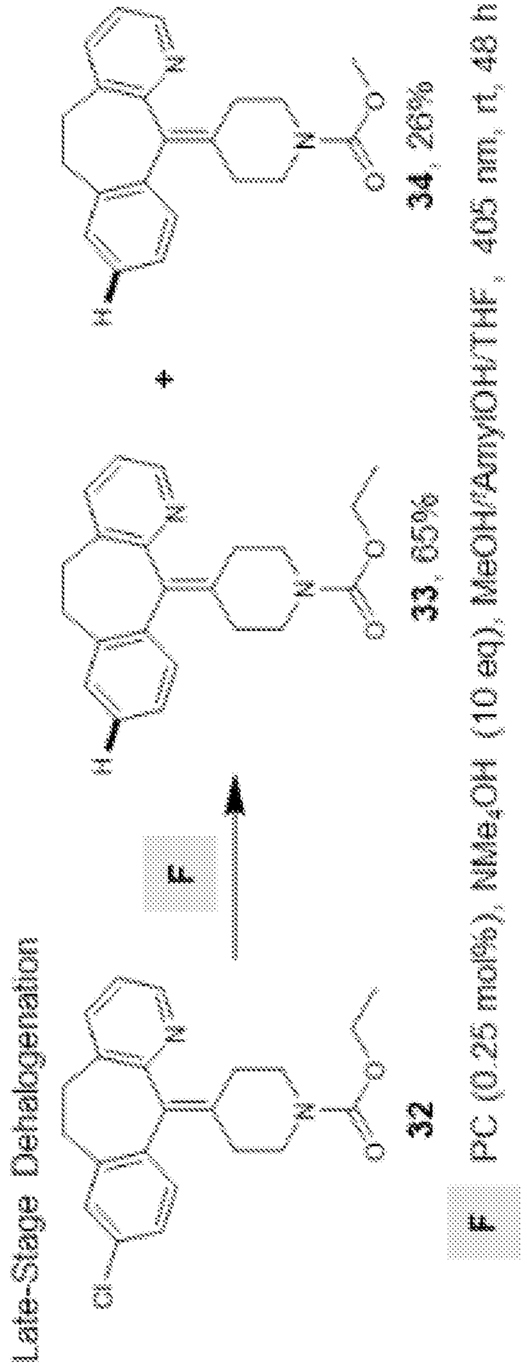

In yet another embodiment, as shown in FIG. 1F, methods of the disclosure may provide for reductive dehalogenation. As illustrated, dehalogenation of the pharmaceutical loratadine may be achieved (33, 65% yield), although significant transesterification also occurs with the solvent (34).

In certain embodiments, the methods may be for the reduction of aromatic compounds (Birch Reductions), such as benzene, benzeneoid, and heteroaromatic compounds, using light as the driving force. The method comprises contacting an aromatic substrate with a sacrificial electron source in the presence of a photoredox catalyst in a solvent, thereby forming a reaction mixture. Exposing the reaction mixture to visible or UV light under reaction condition sufficient to reduce the aromatic substrate compound. In some embodiments, the aromatic compound may be activated or unactivated.

Non-limiting examples of Birch reaction products in accordance with embodiments of the disclosure may be 2-(cyclohexa-1,4-dien-1-yl)ethan-1-ol, 1-pentylcyclohexa-1,4-diene, 1-(cyclohexa-1,4-dien-1-yl)propan-2-ol, 1,4-cyclohexadiene, 1-methyl cyclohexa-1,4-diene, (cyclohexa-1,4-dien-1-ylmethyl)benzene, 3-(cyclohexa-1,4-dien-1-yl) propanoic acid, phenylpropan-3-ol, 3-(cyclohexa-1,4-dien-1-yl)propan-1-ol, 3,4,5,8-tetrahydro-1H-isochromene, 4-phenylbutanoic acid, 4-(cyclohexa-1,4-dien-1-yl)butanoic acid, t-butyl phenylethyl carbamate, tert-butyl (2-(cyclohexa-1,4-dien-1-yl)ethyl)carbamate, 2-(5-methyl cyclohexa-1,4-dien-1-yl)ethan-1-ol, 1,2,3,4,5,8-hexahydronaphthalene, or methyl (2-(5-methylcyclohexa-1,4-dien-1-yl) ethyl)carbamate.

(a) Substrates

In general, the methods of the disclosure may be used in connection with any suitable substrate capable of accepting an electron via a photoredox catalytic reaction in the presence of a photoredox catalyst, e.g., a photoredox catalyst of Formula (I).

Such substrates may include aromatic substrates and those including reactive unsaturated functional groups. In certain embodiments, the aromatic substrate may be activated or unactivated. In certain embodiments, the aromatic substrate may be, but is not limited to, benzene, substituted benzenes, benzeneoids, heteroaromatic compounds, and substituted heteroaromatic compounds.

(b) Photoredox Catalyst

In general, the method as described herein may be performed in the presence of a photoredox catalyst (PC). Any suitable photoredox catalyst may be used in connection with the methods of the disclosure. For instance, in some embodiments, an organic PC of higher triplet energy, although metal complexes may also be used. In certain embodiments, the PC is a compound capable of absorbing light of 365 nm or greater. In certain embodiments, the PC is selected from organic, inorganic, organometallic, or benzo[ghi]perylene monoimide (BPI) compounds. Benzo[ghi]perylene monoimide (BPI) compounds of Formula (I) described herein.

In certain embodiments, the photoredox catalysts (PC) may be a benzo[ghi]perylene monoimide (BPI) compound selected from benzo[ghi]perylene monoimide (BPI) and substitutions and derivatives thereof. By way of non-limiting example, such substitutions and derivatives thereof may include substitutions with hydrogen, halide, alkyl, phenyl, aryl, and substituted aryls. In certain embodiments, the BPI may be substituted with one or more of the following: hydrogen, bromide, phenyl, aryl, alkyl, 4-CN-Ph, 4-$CF_3$-Ph, 4-biphenyl, 4-OMe-Ph, or 4-$N(Me)_2$-Ph, etc.

In certain embodiments, the photoredox catalysts may be selected from: 2-(2-ethylhexyl)-1H-peryleno[1,12-efg] isoindole-1,3(2H)-dione, 6,8,11-tribromo-2-(2-ethylhexyl)-1H-peryleno[1,12-efg]isoindole-1,3(2H)-dione, 4,4',4''-(2-(2-ethylhexyl)-1,3-dioxo-2,3-dihydro-1H-peryleno[1,12-efg]isoindole-6,8,11-triyl)tribenzonitrile, 2-(2-ethylhexyl)-6,8,11-tris(4-(trifluoromethyl)phenyl)-1H-peryleno[1,12-efg]isoindole-1,3(2H)-dione, 2-(2-ethylhexyl)-6,8,11-triphenyl-1H-peryleno[1,12-efg]isoindole-1,3(2H)-dione, 6,8,11-tri([1,1'-biphenyl]-4-yl)-2-(2-ethylhexyl)-1H-peryleno[1,12-efg]isoindole-1,3(2H)-dione, 2-(2-ethylhexyl)-6,8,11-tris(4-methoxyphenyl)-1H-peryleno[1,12-efg]isoindole-1,3(2H)-dione, or 6,8,11-tris(4-(dimethylamino)phenyl)-2-(2-ethylhexyl)-1H-peryleno[1,12-efg]isoindole-1,3(2H)-dione.

Without intending to be limited by theory, the photoredox catalysts may utilize consecutive photoinduced electron transfer in order to harness the power of two photons of visible light. These catalysts possess excited state reduction potentials great enough to perform photoinduced electron transfer to aromatic compounds, resulting in, e.g., 1,4-cyclohexadiene products. As described herein, in accordance with aspects of the disclosure, the mechanistic pathway was investigated, revealing an unexpected Meisenheimer complex intermediate.

Generally, the amount of photoredox catalyst used in the method may be range from about 0.1 mol % to about 1.5 mol %, based on the total volume of reaction mixture. In various embodiments, the amount of photoredox catalyst in the reaction mixture may be about 0.1 mol % to about 1.2 mol %, about 0.1 mol % to about 1.0 mol %, about 0.1 mol % to about 0.75 mol %, etc, based on the total volume of reaction mixture. In various embodiments, additional catalyst may be added or supplemented to the reaction mixture after an initial reaction time to maintain sufficient reactivity.

(c) Sacrificial Electron Donor

The method, as disclosed herein, utilizes a sacrificial electron donor. The sacrificial electron donor may be an organic or an inorganic compound. In other embodiments, the sacrificial electron donor may be provided via an electrochemical device. Any suitable electrochemical device capable of generating an electrical current may be used, e.g., an electrode, a battery, an electrical wire, etc.

Suitable sacrificial donor sources may be sulfides, nitrites, ferrous salts, carbon dioxide, alcohols, organic acids, formaldehyde, amines, and the like. Non-limiting examples may be oxalic acid, formic acid, formaldehyde, triethylamine, tetramethylammonium fluoride, tetrabutylammonium fluoride, tetramethylammonium hydroxide, tetraethyl ammonium hydroxide, tetrabutylammonium hydroxide, and tetrahexylammonium hydroxide. In one preferred embodiment, the sacrificial electron donor is tetramethylammonium hydroxide.

In general, the equivalent amount of the sacrificial electron donor may range from about 1.0 equivalent to 15.0 equivalents as compared to the aromatic substrate. In various embodiments, the equivalent amount of the sacrificial electron donor may range from about 1.0 equivalent to 15.0 equivalents, from about 2.0 equivalents to about 12.0 equivalents, or from about 5.0 equivalents to about 10.0 equivalents as compared to the aromatic substrate. In one preferred embodiment, the equivalent amount of the sacrificial electron donor may be about 8.0 equivalents as compared to the aromatic substrate.

(d) Solvent

The method further comprises a solvent. The solvent provides a proton to the radical anion and the anion that is formed. The solvent comprises an alcohol or a mixture of alcohols. Non-limiting examples of suitable alcohols may be methanol, iso-propanol, t-butanol, t-amyl alcohol, ethylene glycol, or a combination thereof. In one preferred embodiment, the solvent for the method comprises a mixture of methanol and t-amyl alcohol.

Generally, the equivalent amount of the solvent may range from about 4.0 equivalents to 15.0 equivalents as compared to the aromatic substrate. In various embodiments, the equivalent amount of the solvent may range from about 4.0 equivalents to 15.0 equivalents, from about 5.0 equivalents to about 12.0 equivalents, or about 7 equivalents to about 10 equivalents as compared to the aromatic substrate.

(e) Light

In general, the reduction reaction of the disclosure is performed in the presence of light. In some embodiments, the light may be visible light or UV light.

In an embodiment, visible light may be from about 360 nm to about 740 nm. In other embodiments, visible light may be from about 360 nm to about 500 nm, about 365 nm to about 500 nm, or about 365 nm to about 457 nm. In an exemplary embodiment, the reaction may be performed in the presence of visible light at about 365 nm, 395 nm, 405 nm, 457 nm, etc.

In an embodiment, UV light may be from about 10 nm to about 400 nm. In other embodiments, UV light may be from about 100 nm to about 400 nm, about 200 nm to about 400 nm, about 300 nm to about 400 nm, about 350 nm to about 400 nm, about 365 nm to about 400 nm, etc. In an exemplary embodiment, the reaction may be performed in the presence of UV light at about 365 nm.

In other embodiments, the light may be from about 300 nm to about 1000 nm. In some embodiments, the light may range from about 300 nm to about 1000 nm, about 300 nm to about 900 nm, about 300 nm to about 800 nm, about 300 nm to about 700 nm, about 300 nm to about 600 nm, about 300 nm to about 500 nm, or about 300 nm to about 400 nm.

(f) Reaction Conditions

In general, method will be conducted at a temperature that ranges from about room temperature (~23° C.) to about 80° C. In various embodiments, the temperature of the reaction may range from about room temperature to about 80° C., from about 30° C. to about 70° C., or from about 40° C. to about 60° C. In one embodiment, the reaction may be conducted at temperature that ranges from about 10° C. to about 40° C., or from about 20° C. to about 30° C. In another embodiment, the temperature of the reaction may be about room temperature (~23° C.). The reaction typically is performed under ambient pressure. The reaction is conducted under an inert atmosphere, for example under nitrogen, argon or helium.

Generally, the reaction is allowed to proceed for a sufficient period of time until the reaction is complete, as determined by any method known to one skilled in the art, such as HPLC or proton nuclear magnetic resonance (e.g., $^{1}H$ NMR). The duration of the reaction may range from about 30 minutes to about 150 hours, from about 30 minutes to about 144 hours, from about 30 minutes to about 100 hours, about 10 hours to about 100 hours, about 24 hours to about 100 hours, about 48 hours to about 100 hours, etc. In yet other embodiments, the reaction occurs for at least about 10 hours, at least about 24 hours, at least about 72 hours, or at least about 96 hours.

Generally, methods of the disclosure may be performed under reaction conditions sufficient to result in about 10% conversion. In various embodiments, methods of the disclosure may be performed under reaction conditions sufficient to result in about 10% conversion, at least about 15% conversion, at least about 20% conversion, at least about 25% conversion, at least about 50% conversion, at least about 55% conversion, at least about 60% conversion, at least about 65% conversion, at least about 70% conversion, at least about 75% conversion, at least about 80% conversion, at least about 85% conversion, at least about 90% conversion, at least about 93% conversion, at least about 95% conversion, at least about 97% conversion, at least about 98% conversion.

(III) Methods for Preparing the Compound Comprising Formula (I) or a Salt Thereof Another aspect of the present disclosure encompasses methods for preparing the photoredox catalyst of Formula (I) or a salt thereof:

Formula (I)

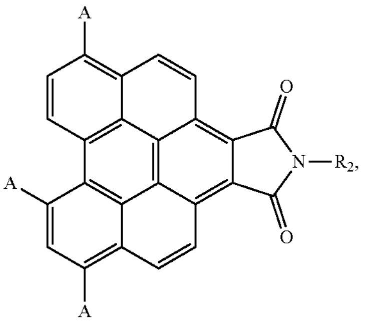

the method comprising:

(a) contacting the compound of Formula (II):

Formula (II)

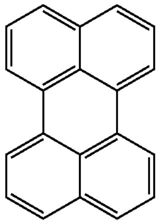

;

with maleic anhydride and p-chloroanil to form the compound comprising Formula (III):

Formula (III)

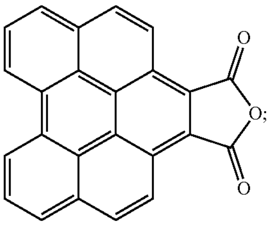

(b) contacting the compound comprising Formula (III) with an aliphatic amine to form the compound comprising Formula (IV):

Formula (IV)

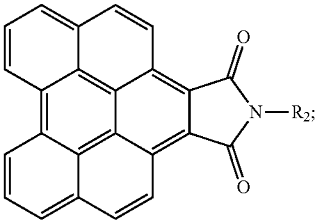

(c) contacting the compound comprising Formula (IV) with a halogenating agent to form the compound comprising Formula (V);

Formula (V)

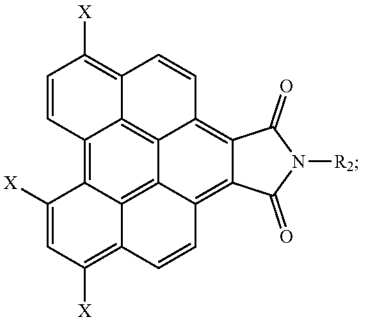

and (d) contacting the compound comprising Formula (V) with an aryl boronic acid in the presence of a catalyst to form the photoredox catalyst comprising Formula (I) or a salt therof.

Figure 2:
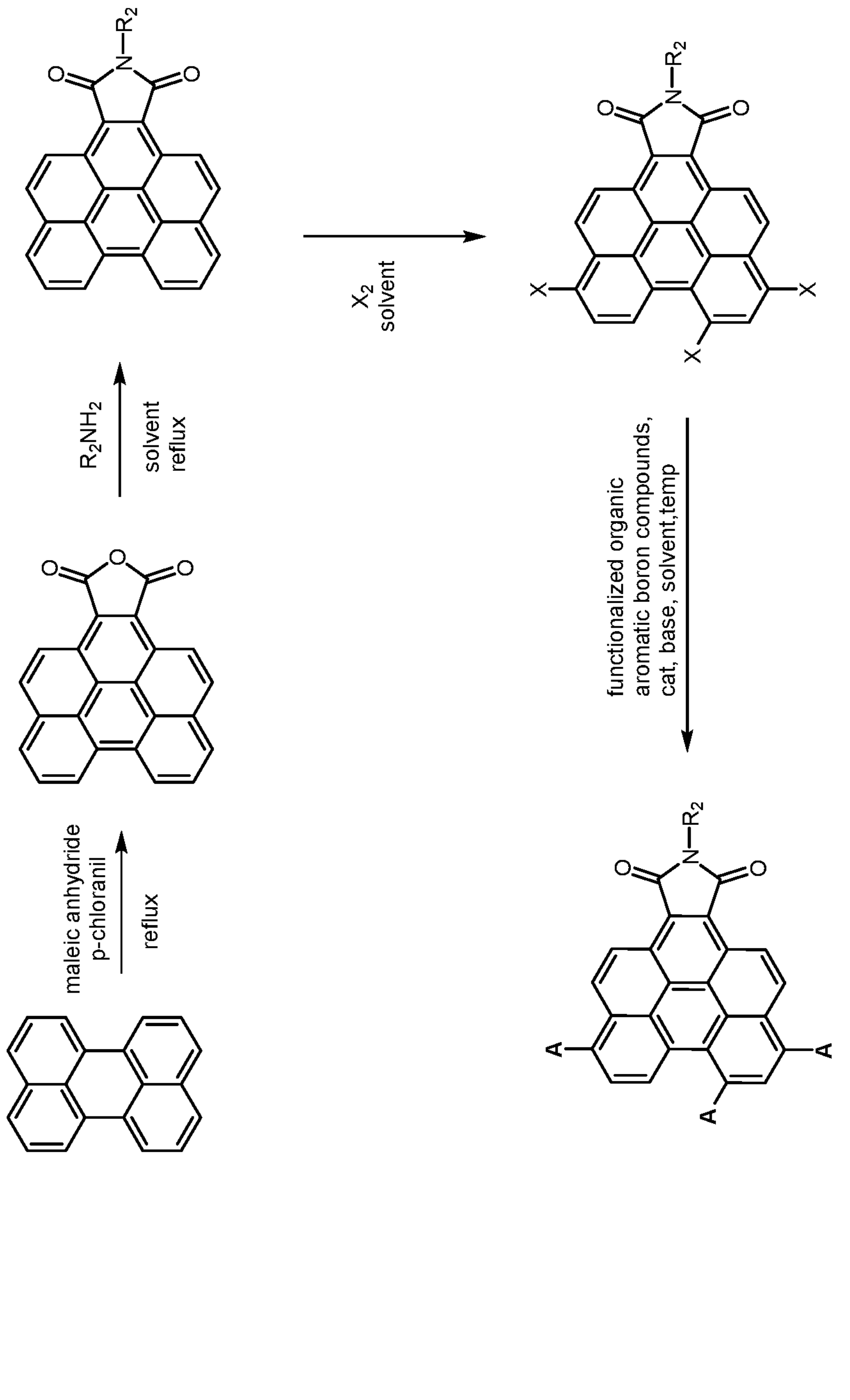
FIG. 2 illustrates a general Reaction Scheme in accordance with embodiments of the disclosure for making photoredox catalysts of Formula (I).
Figures 3A, 3B, 3C, 3D:
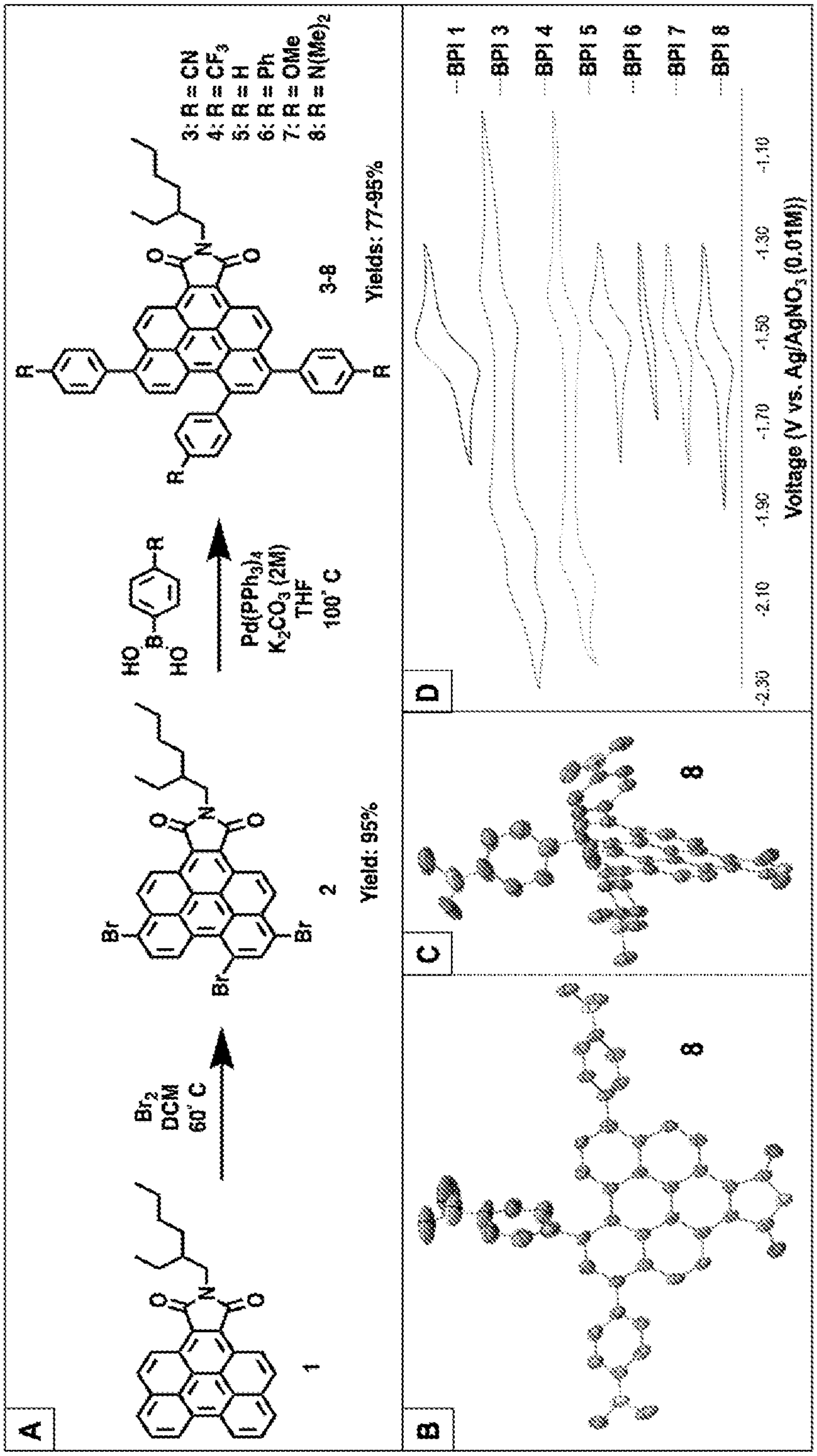
FIG. 3A-3D. (A) illustrates an exemplary Reaction Scheme, in accordance with embodiments of the disclosure of BPI photoredox catalysts. (B) Top view and (C) side view of the X-ray crystal structure of BPI 8. The 2-ethyl hexyl substituent and hydrogen atoms are omitted for clarity. ORTEP plots with anisotropic displacement parameters set at 50% probability. Atoms are represented as the following colors: carbon, grey; nitrogen, blue; oxygen, red. (D) Cyclic voltammetry traces showing the reversible reductions of BPIs 1 and 3-8

Generally, in accordance with embodiments of the Reaction Scheme depicted in FIG. 2, A is selected from —H, an optionally substituted $C_1$ to $C_{16}$ alkyl, an optionally substituted aryl, or an optionally substituted heteroaryl; $R_2$ is selected from an optionally substituted $C_1$ to $C_{16}$ alkyl, an optionally substituted aryl, or an optionally substituted heteroaryl; and X is selected from a group consisting of chloride, bromide, or iodide.

In some embodiments, A may be selected from:

A = $R_1$;

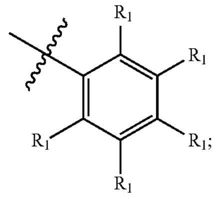

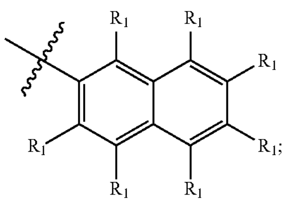

or

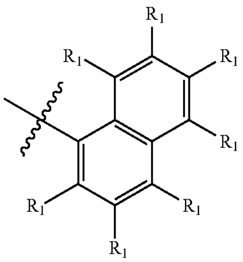

wherein:

$R_1$ is selected from —H, halogen, —CN, —$OR_3$, $NR_4R_5$, $C_1$ to $C_8$ substituted alkyl, $C_1$ to $C_8$ unsubstituted alkyl, substituted aryl, unsubstituted aryl, substituted heteroaryl, or unsubstituted heteroaryl.

In some embodiments, $R_1$ is selected from —H, $C_1$-$C_6$ alkyl, $C_1$-$C_6$ haloalkyl, optionally substituted phenyl, —OH, —O($C_1$-$C_6$ alkyl), —$NO_2$, —CN, —C(═O)OH, —C(═O)O($C_1$-$C_6$ alkyl), —C(═O)O-phenyl, —C(═O)($C_1$-$C_6$ alkyl), —C(═O)-phenyl, —$S(O)_2NH_2$, —$S(O)_2NH$($C_1$-$C_6$ alkyl), —$S(O)_2N$($C_1$-$C_6$ alkyl)($C_1$-$C_6$ alkyl), —S($C_1$-$C_6$ alkyl), —S(O)($C_1$-$C_6$ alkyl), —$S(O)_2$($C_1$-$C_6$ alkyl), —S(phenyl), —S(O)(phenyl), and —$S(O)_2$(phenyl). In some embodiments, $R_1$ is selected from a group consisting of —H, halogen, —CN, —$OR_3$, —$NR_4R_5$, $C_1$-$C_4$ substituted alkyl, $C_1$-$C_4$ unsubstituted alkyl, substituted aryl, unsubstituted aryl, substituted heteroaryl, or unsubstituted heteroaryl. In certain embodiments, $R_1$ is selected from a group consisting of —H, fluoride, chloride, bromide, —CN, —$OR_3$, —$NR_4R_5$, methyl, ethyl, n-propyl, iso-propyl, n-butyl, sec-butyl, iso-butyl, t-butyl, —$CCl_3$, —$CF_3$, phenyl, 1-napthyl, 2-napthyl, and 1-napthyl and 2-napthyl substituted with an $R_3$ group. In specific embodiments, $R_1$ is selected from a group consisting of —H, bromide, —CN, —$OR_3$, —$NR_4R_5$, —$CF_3$, or phenyl.

In general, in accordance with embodiments of the Reaction Scheme depicted in FIG. 2, $R_2$ is selected from $C_1$ to $C_{16}$ substituted alkyl, $C_1$ to $C_{16}$ unsubstituted alkyl, substituted aryl, unsubstituted aryl, substituted heteroaryl, or unsubstituted heteroaryl. In some embodiments, $R_2$ is selected from a $C_1$ to $C_{16}$ substituted or unsubstituted alkyl. In some embodiments, $R_2$ is selected from a $C_1$ to $C_{12}$ substituted or unsubstituted alkyl. In certain embodiments, $R_2$ is selected from a $C_1$ to $C_8$ substituted or unsubstituted alkyl. In specific embodiments, $R_2$ is 2-ethylhexyl. In other embodiments, $R_2$ is selected from a substituted or unsubstituted phenyl. In other embodiments, $R_2$ is selected from a substituted or unsubstituted napthyl, e.g., 1-napthyl or 2-napthyl.

Generally, in accordance with embodiments of the Reaction Scheme depicted in FIG. 2, $R_3$ is selected from —H, —$NR_4R_5$, $C_1$ to $C_8$ substituted alkyl, or $C_1$ to $C_8$ unsubstituted alkyl, substituted aryl, unsubstituted aryl, substituted heteroaryl, or unsubstituted heteroaryl. In some embodiments, $R_3$ is selected from a —H, $C_1$ to $C_8$ substituted alkyl, or $C_1$ to $C_8$ unsubstituted alkyl. In some embodiments, $R_3$ is selected from H, $C_1$ to $C_4$ substituted alkyl, or $C_1$ to $C_4$ unsubstituted alkyl. In certain embodiments, $R_3$ is selected from H, methyl, ethyl, n-propyl, iso-propyl, n-butyl, sec-butyl, iso-butyl, or t-butyl. In specific embodiments, $R_3$ is methyl.

In general, in accordance with embodiments of the Reaction Scheme depicted in FIGS. 2, $R_4$ and $R_5$ are each independently selected from —H, $C_1$ to $C_8$ substituted alkyl, $C_1$ to $C_8$ unsubstituted alkyl, substituted aryl, unsubstituted aryl, substituted heteroaryl, or unsubstituted heteroaryl. In some embodiments, $R_4$ and $R_5$ are independently selected from H, $C_1$ to $C_8$ substituted alkyl, or $C_1$ to $C_8$ unsubstituted alkyl. In some embodiments, $R_4$ and $R_5$ are independently selected from H, $C_1$ to $C_4$ substituted alkyl, or $C_1$ to $C_4$ unsubstituted alkyl. In certain embodiments, $R_4$ and $R_5$ are independently selected from H, methyl, ethyl, n-propyl, iso-propyl, n-butyl, sec-butyl, iso-butyl, or t-butyl. In specific embodiments, $R_4$ and $R_5$ are H or methyl.

Generally, in accordance with embodiments of the Reaction Scheme depicted in FIG. 2, X is selected from chloride, bromide, or iodide. In some embodiments, X is selected from a group consisting of chloride, bromide, or iodide. In certain embodiments, X is either chloride or bromide. In specific embodiments, X is bromide.

(a) Anhydride Formation of Step (a)

As discussed above, Step (a) of the four-step method involves contacting the compound comprising Formula (II) with maleic anhydride and chloroanil forming an anhydride. This reaction step in the method is referred to as a "Diels Alder reaction."

The compound comprising Formula (II) is detailed above. Non-limiting examples of the compound comprising Formula (II) may be perylene.

Generally, the equivalent ratio of maleic anhydride to perylene ranges from about 1:1 to about 100:1. In various embodiments, the equivalent ratio of maleic anhydride to benzo[ghi]perylene ranges from about 1:1 to about 100:1, from about 10:1 to about 75:1, or from about 30:1 to about 50:1. In one preferred embodiment, the equivalent ratio of maleic anhydride to benzo[ghi]perylene may be about 40:1.

In general, the equivalent ratio of p-chloroanil to perylene ranges from about 1:1 to about 5:1. In various embodiments, the equivalent ratio of p-chloroanil to perylene ranges from about 1:1 to about 5:1, from about 1.5:1 to about 4:1, or from about 2:1 to about 3:1. In one preferred embodiments, the equivalent ratio of p-chloroanil to perylene may be about 2.3:1.

Step (a), as detailed herein, may comprise a solvent or may be conducted neat. As recognized by those of skill in the art, the solvent can and will vary depending on the starting substrates in the process. The solvent may be a polar protic solvent, a polar aprotic solvent, a non-polar solvent, or combinations thereof. Suitable examples of polar protic solvents include, but are not limited to, water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethyl acetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. In one exemplary embodiment, step (a) is conducted neat.

In general, the volume to weight ratio of the solvent to the compound comprising Formula (I) will range from about 0.5:1 to about 500:1. In various embodiments, the volume to weight ratio of the solvent to the compound comprising Formula (I) may range from about 0.5:1 to about 500:1, from about 2:1 to about 250:1, from about 5:1 to about 200:1, or from about 10:1 to about 100:1.

In general, the reaction of step (a) will be conducted at a temperature that ranges from about 150° C. to about 220° C. depending on the solvent utilized or the reaction is conducted neat. In various embodiments, the temperature of the reaction may range from about 150° C. to about 220° C., from about 170° C. to about 220° C., or from about 190° C. to about 210° C. In one embodiment, the reaction may be conducted at temperature that ranges from about 190° C. to about 210° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 2 hours. In various embodiments, the duration of the reaction may range from about 5 minutes to about 2 hours, from about 5 minutes to about 1 hour, or from about 5 minutes to 30 minutes. In an exemplary embodiment, the reaction may be allowed to proceed for about 10 minutes to about 15 minutes. In this context, a "completed reaction" generally means that the reaction mixture contains a significantly diminished amount of the compound of Formula (II). Typically, the amount of the compound of Formula (II) remaining in the reaction mixture at the end of the reaction may be less than about 10%, less than about 5%, or less than about 2%.

The compound comprising Formula (III) may have a yield of at least about 60%. In various embodiments, the compound comprising Formula (II) may have a yield of at least about 60%, at least about 65%, at least about 70%, at least about 75%, at least about 80%, at least about 85%, at least about 90%, at least about 95%, or at least about 99%.

(b) Imide Formation of Step (b)

Step (b) of the four-step method comprising contacting the compound comprising Formula (III) with a substituted or unsubstituted aliphatic amine forming the compound comprising Formula (IV). This step converts the cyclic anhydride into a cyclic imide.

The compound comprising Formula (III) and Formula (IV) are detailed above and herein. In some embodiments, $R_2$ is selected from a group consisting of $C_1$ to $C_{12}$ substituted or unsubstituted alkyl. In certain embodiments, $R_2$ is selected from a group consisting of $C_1$ to $C_8$ substituted or unsubstituted alkyl. In specific embodiments, $R_2$ is 2-ethylhexyl.

In general, the equivalent ratio of the substituted or unsubstituted aliphatic amine to the compound comprising Formula (III) may range from about 1:1 to about 3:1. In various embodiments, the equivalent ratio of the substituted or unsubstituted aliphatic amine to the compound comprising Formula (III) may range from about 1:1 to about 3:1, from about 1.1 to about 2.5:1, or from about 1.4:1 to about 1.6:1. In one preferred embodiment, the equivalent ratio of the substituted or unsubstituted aliphatic amine to the compound comprising Formula (III) may be about 1.5:1.

Step (b), as detailed herein, may comprise a solvent. Suitable solvents are detailed above in Section (III)(a). In one preferred embodiment, Step (b) is conducted in DMF In general, the volume to weight ratio of the solvent to the compound comprising Formula (III) will range from about 0.5:1 to about 500:1. In various embodiments, the volume to weight ratio of the solvent to the compound comprising Formula (III) may range from about 0.5:1 to about 500:1, from about 2:1 to about 250:1, from about 5:1 to about 200:1, or from about 10:1 to about 100:1. In one preferred embodiment, the volume to weight ratio of the solvent to the compound comprising Formula (III) may be about 150:1.

Generally, the reaction is allowed to proceed for a sufficient period of time until the reaction is complete, as determined by any method known to one skilled in the art, such as HPLC or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an exemplary embodiment, the reaction may be allowed to proceed for about 16 hours. In this context, a "completed reaction" generally means that the reaction mixture contains a significantly diminished amount of the compound of Formula (III). Typically, the amount of the compound of Formula (III) remaining in the reaction mixture at the end of the reaction may be less than about 10%, less than about 5%, or less than about 2%.

The compound comprising Formula (IV) may have a yield of at least about 60%. In various embodiments, the compound comprising Formula (II) may have a yield of at least about 60%, at least about 65%, at least about 70%, at least about 75%, at least about 80%, at least about 85%, at least about 90%, at least about 95%, or at least about 99%.

(c) Halogenation of the Compound Comprising Formula (IV)

As discussed above, Step (c) of the four-step process involves contacting the compound comprising Formula (IV) with halogenating agent. Contacting between the compound comprising Formula (IV) with the halogenating agent entails substituting three halogen atoms for three hydrogens on the benzo[ghi]perylene ring forming the compound comprising Formula (V).

The compound comprising Formula (IV) and Formula (V) are detailed above and herein. In some embodiments, X is selected from a group consisting of chloride, bromide, or iodide. In certain embodiments, X is either chloride or bromide. In specific embodiments, X is bromide.

A number of useful halogenation agents may be used in Step (b) of the process. Non-limiting examples of these halogenating agents may be N-chlorosuccinimide, N-bromosuccinimide, N-iodosuccinimide, chlorine, bromine, or iodine. In one preferred embodiment, the halogenation agent used in Step (c) is bromine.

As appreciated by the skilled artisan, the reaction halogenates three positions on the benzo[ghi]perylene ring. Generally, the equivalent ratio of the compound comprising Formula (IV) and the halogenation reagent may range from about 1:1 to about 1:50. In various embodiments, the equivalent ratio of the compound comprising Formula (IV) and the halogenation reagent may range from about 1:1 to about 1:50, from about 5:1 to about 40:1, from about 10:1 to about 40:1, or from about 25:1 to about 35:1.

Step (c) of the process further comprises a solvent. Solvents are listed above in step (a). In one preferred embodiment, the solvent useful in the halogenation reaction is dichloromethane (DCM).

In general, the volume to weight ratio of the solvent to the compound comprising Formula (IV) may range from about 1:1 to about 100:1. In various embodiments, the volume to weight ratio of the solvent to the compound comprising Formula (IV) may range from about 1:1 to about 100:1.0, from about 5.0 to about 75.0:1.0, from about 10.0:1.0 to about 60.0:1.0, or from about 20.0:1.0 to about 50.0:1.0. In one preferred embodiment, the volume to weight ratio of the solvent to the compound comprising Formula (IV) may be about 50:1.

In general, the reaction of Step (c) will be conducted at a temperature that ranges from about room temperature (~23° C.) to about 100° C. In various embodiments, the temperature of the reaction may range from about 23° C. to about 100° C., from about 30° C. to about 90° C., from about 40° C. to about 80° C., or from about 50° C. to about 60° C. In one embodiment, the reaction may be conducted at temperature that ranges from about 50° C. to about 60° C. The reaction typically is performed in a bomb flask. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC or proton nuclear magnetic resonance (e.g., $^1$H NMR). The duration of the reaction may range from about 24 hours to about 7 days. In various embodiments, duration of the reaction may range from about 24 hours to about 7 days, from about 2 days to about 6 days, or from about 3 days to 5 days. In this context, a "completed reaction" generally means that the reaction mixture contains a significantly diminished amount of the compound of Formula (IV). Typically, the amount of the compound of Formula (IV) remaining in the reaction mixture at the end of the reaction may be less than about 10%, less than about 5%, or less than about 2%.

The compound comprising Formula (V) may have a yield of at least about 60%. In various embodiments, the compound comprising Formula (V) may have a yield of at least about 60%, at least about 65%, at least about 70%, at least about 75%, at least about 80%, at least about 85%, at least about 90%, at least about 95%, or at least about 99%.

(d) Cross Coupling of the Compound Comprising Formula (V)

As discussed above, Step (d) of the four-step process involves contacting the compound comprising formula (V) with a functionalized organic aromatic boron compound in the presence of a catalyst and a base. Contacting between the compound comprising Formula (V) with organic aromatic boron compound, a catalyst, and a base entails substituting three halogen atoms for three aromatic groups on the benzo[ghi]perylene ring forming the compound comprising Formula (I). As appreciated by the skilled artisan, this process step is termed a "Suzuki Cross-Coupling Reaction" or a "Suzuki-Miyaura Cross-Coupling Reaction."

The compound comprising Formula (V) is described in more detail herein and above.

A wide variety of functionalized organic aromatic boron compounds may be used in step (d). These organic aromatic boron compounds may be boronic acids, boronic acid ester, a protected boronic acid, or trifluoroborates. Non-limiting examples of useful functionalized organic aromatic boron compounds may be 4-biphenylboronic acid, 4-cyanophenylboronic acid, 4-fluorophenylboronic acid, 4-methoxyphenylboronic acid, 4-trifluorophenylboronic acid, phenylboronic acid, or 4-methoxybenzeneboronic acid.

In general, the mole ratio of the compound comprising Formula (V) to the organic aromatic boron compound may range from about 1.0:2.0 to about 1.0:10.0. In various embodiments, the mole ratio of the compound comprising Formula (V) to the organic aromatic boron compound may range from about 1.0:2.0 to about 1.0:10.0, from about 1.0:3.0 to about 1.0:8.0, from about 1.0:4.0 to about 1.0:6.0. In one embodiment, the mole ratio of the compound comprising Formula (V) to the functionalized organic aromatic boron compound may be about 1.0:6.0.

The process as detailed above, utilized a catalyst. The catalyst can comprise a palladium catalyst or a nickel catalyst. In various embodiments, the catalyst useful in Step (d) may further comprises a ligand. Non-limiting of suitable catalysts may be $Pd(OAc)_2$, $Pd(OCOCF_3)_2$, $Pd(PPh_3)_2C_{12}$, $Pd(PPh_3)_4$, or $Ni(PPh_3)_2Cl_2$. Non-limiting examples of suitable ligands may be $PPh_3$, $P(o\text{-tolyl})_3$, BINAP, BINAM. In one preferred embodiment, the catalyst is $Pd(PPh_3)_4$ In general, the mole ratio of the compound comprising Formula (V) to the catalyst may range from 1.0:0.001 to about 1.0:0.15. In various embodiments, the mole ratio of the catalyst to the compound comprising Formula (V) may range from 1.0:0.001 to about 1.0:0.15, from about 1.0: 0.005 to about 1.0:0.14, or from about 1.0:0.01 to about 1.0:0.10. In one embodiment, the mole ratio of the catalyst to the compound comprising Formula (V) is about 1.0:0.15.

Generally, if the catalyst utilizes a ligand, the mole ratio of the catalyst to the ligand may range from about 1.0:0.5 to about 1.0:5.0. In various embodiments, the mole ratio of the catalyst to the ligand may range from about 1.0:0.5 to about 1.0:5.0, from about 1.0:1.0 to about 1.0:4.0, or from about 1.0:1.5 to about 1.0:3.0.

The process detailed above further comprises a base. The base may be a solid base or dissolved in water at various concentrations. Non-limiting examples of suitable bases may be NaOt-Bu, LHMDS, $Cs_2CO_3$, $K_3PO_4$, or $K_2CO_3$. In one preferred embodiment, the base useful in Step (d) is $K_2CO_3$.

In general, the equivalent ratio of the base to the compound comprising Formula (V) to the base may range from about 1:1 to about 100:1. In various embodiments, the equivalent ratio of the base to the compound comprising Formula (V) to the base may range from about 1:1 to about 100:1, from about 10:1 to about 75:1, or from about 30:1 to about 50:1.

Step (d) of the process further comprises a solvent. Solvents are listed above in Step (a). In one preferred embodiment, the solvent useful in the halogenation reaction is tetrahydrofuran (THF) in a mixture with water.

In general, the volume to weight ratio of the solvent to the compound comprising Formula (V) will range from about 1:1 to about 500:1. In various embodiments, the volume to weight ratio of the solvent to the compound comprising Formula (V) may range from about 1:1 to about 500:1, from about 10:1 to about 300:1, from about 50:1 to about 200:1, or from about 75:1 to about 125:1.

In general, the reaction of step (d) will be conducted at a temperature that ranges from about 25° C. to about 150° C. In various embodiments, the temperature of the reaction may range from about 25° C. to about 150° C., from about 50° C. to about 130° C., from about 75° C. to about 120° C., or from about 90° C. to about 1000° C. In one embodiment, the reaction may be conducted at temperature of about 100° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC or proton nuclear magnetic resonance (e.g., $^1H$ NMR). The duration of the reaction may range from about 5 minutes to about 72 hours. In some embodiments, the duration of the reaction may range from about 5 minutes to about 72 hours, from about 1.0 hour to about 60 hours, from about 12 hours to about 55 hours, or from about 30 hours to about 50 hours. In an exemplary embodiment, the reaction may be allowed to proceed for about 24 hours. In this context, a "completed reaction" generally means that the reaction mixture contains a significantly diminished amount of the compound of Formula (V). Typically, the amount of the compound of Formula (V) remaining in the reaction mixture at the end of the reaction may be less than about 10%, less than about 5%, or less than about 2%.

The compound comprising Formula (I) may have a yield of at least about 60%. In various embodiments, the compound comprising Formula (I) may have a yield of at least about 60%, at least about 65%, at least about 70%, at least about 75%, at least about 80%, at least about 85%, at least about 90%, at least about 95%, or at least about 99%.

EXAMPLES

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described methods without departing from the scope of the invention, it is intended that all matter contained in the above description and in the examples given below, shall be interpreted as illustrative and not in a limiting sense.

Methods and Materials

All purchased reagents were used without further purification. NMR spectra were recorded on a Varian 300 MHz, 400 MHz, or 500 MHz NMR Spectrometer as noted for all characterizations. All $^1H$ NMR are reported in δ units (parts per million-ppm) and were measured relative to the signals found in residual chloroform (7.26 ppm). All $^{13}C$ NMR were measured relative to $CDCl_3$ (77.16 ppm).

The photoreactors used were custom designed and built in-house and the specifications have been published previously. All LEDs were purchased from LED Engine and full emission spectra, as well as peak wavelength shift vs. temperature data, are available online in the respective manufacturer datasheets. In the photoreactor, 405 nm, 457 nm, cool white, 523 nm, and 590 nm LEDs were run at 700 mA and a forward voltage of 13.5 V, while 365 nm and 395 nm LEDs were run at 700 mA and a forward voltage of 15.5 V.

Example 1: Preparation of Benzo[ghi]perylene-1,2-dicarboxylic Anhydride

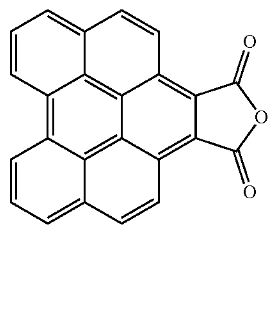 [SMILES: O=c1oc(=O)c2c3ccc4cccc5c6cccc7ccc(c12)c(c76)c3c45]

Perylene (5.1 g, 20 mmol, 1.0 eq.) was dissolved in molten maleic anhydride (80 g, 800 mmol, 40 eq.) at 240 C. p-chloranil (11.2 g, 45.6 mmol, 2.3 eq.) was then slowly added and the mixture was refluxed for 10 minutes. Xylenes (100 mL) was then added and the flask was cooled to room temperature. The red solids were collected by filtration and then refluxed in 2:1 EtOAc:$CHCl_3$ overnight before being filtered while hot. The product was used without further purification.

Example 2: Preparation of 2-(2-Ethylhexyl)-1H-peryleno[1,12-efg]isoindole-1,3(2H)-dione (1)

1

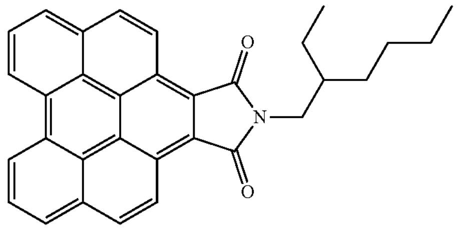

Benzo[ghi]perylene-1,2-dicarboxylic anhydride (0.9 g, 2.6 mmol, 1.0 eq) and a stir bar were added to a 250 mL round bottom flask followed by 150 mL of DMF. 2-Ethyl-1-hexylamine (0.6 mL, 3.9 mmol, 1.5 eq.) was added and the reaction was heated to 125° C. for 16 hours. The reaction was cooled down and 60 mL of concentrated HCl was added to the solution and a yellow-brown solid precipitated from solution. The solid was filtered and then washed with 300 ml of 1M KOH solution, followed by deionized water until a neutral pH was obtained to give an orange powder. The orange powder was recrystallized using DCM/MeOH. Yield: 0.86 g, 72% yield. $^1$H NMR (300 MHz, Chloroform-d) δ=8.23-8.16 (m, 4H), 7.61-7.55 (m, 4H), 7.34 (d, J=9.0 Hz, 2H), 3.60 (d, J=7.1 Hz, 2H), 1.97-1.85 (m, 1H), 1.55-1.35 (m, 8H), 1.05 (t, J=7.3 Hz, 3H), 0.98 (t, J=6.7 Hz, 3H). $^{13}$C NMR (300 MHz, Chloroform-d) δ=169.28, 130.55, 128.45, 128.20, 126.20, 124.43, 122.35, 122.21, 121.79, 121.36, 120.22, 41.57, 39.10, 30.88, 28.86, 24.16, 23.33, 14.36, 10.71. DART: Calculated for $C_{32}$H27$NO_2$ ([M+H+]) 458.2115, found 458.2118.

Example 3: Preparation of 6,8,11-Tribromo-2-(2-ethylhexyl)-1H-peryleno[1,12-efg]isoindole-1,3(2H)-dione (2)

2

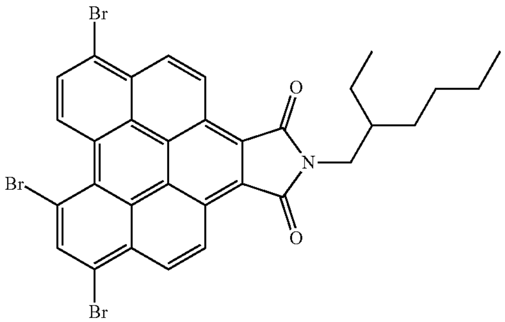

To a 100 mL thick walled flask was added 1 (0.6 g, 1.3 mmol, 1.0 eq.) and stir bar. DCM was added to the solids then heated up to 60° C. until the solid was fully dissolved (~40 mL). After which bromine (2.0 mL, 39 mmol, 30 eq.) was added quickly. The bomb flask was capped and the reaction went from orange to a dark red. After 4 days, the reaction was concentrated and the bromine blown off. The product was recrystallized in DCM and filtered and washed further with hexanes to give a yellow solid. Yield: 0.82 g, 91%. $^1$H NMR (300 MHz, Chloroform-d) δ=8.42 (d, J=8.7 Hz, 1H), 8.01 (d, J=8.9 Hz, 1H), 7.98 (d, J=8.9, 1H), 7.66 (s, Hz, 1H), 7.45 (d, J=9.0 Hz, 1H), 7.30 (d, J=9.0 Hz, 1H), 7.24 (d, J=8.8 Hz, 1H), 3.56 (d, J=7.1 Hz, 2H), 1.93-1.77 (m, 1H), 1.55-1.33 (m, 8H), 1.07-0.93 (m, 6H). $^{13}$C NMR (75 MHz, Chloroform-d) δ=168.26, 168.17, 138.05, 129.08, 127.39, 127.32, 127.23, 126.64, 124.80, 124.44, 124.29, 123.94, 122.97, 122.84, 122.69, 122.56, 122.46, 122.22, 121.98, 121.71, 121.55, 120.99, 116.33, 42.08, 38.94, 30.85, 28.80, 24.14, 23.35, 14.39, 10.70. HRMS (ESI): Calculated for $C_{32}H_{24}Br_3NO_2$ ([M+]) 694.9321, found 694.9332.

Example 4: General Procedure for the Synthesis of Triaryl Substituted BPIs

To a 100 mL flask was added 2 (0.23 g, 0.32 mmol, 1.0 eq.) and boronic acid (2.0 mmol, 6.0 eq.). The flask was then moved into a N2 filled glovebox where $Pd(PPh_3)_4$ (0.06 g, 0.005 mmol, 15 mol %) was added. 25 mL of THF was then added and the flask was removed from the glovebox. 6.2 mL of 2M aqueous $K_2CO_3$ was then added. The reaction was then heated to 100° C. for 24 hours. Dichloromethane (DCM) was added to the mixture and washed with water 3 times, then brine, and dried with $MgSO_4$. All compounds were purified by column chromatography using a gradient of hexanes:toluene as an eluent.

Example 5: Preparation of 4,4',4"-(2-(2-ethylhexyl)-1,3-dioxo-2,3-dihydro-1H-peryleno[1,12-efg]isoindole-6,8,11-triyl)tribenzonitrile (3)

3

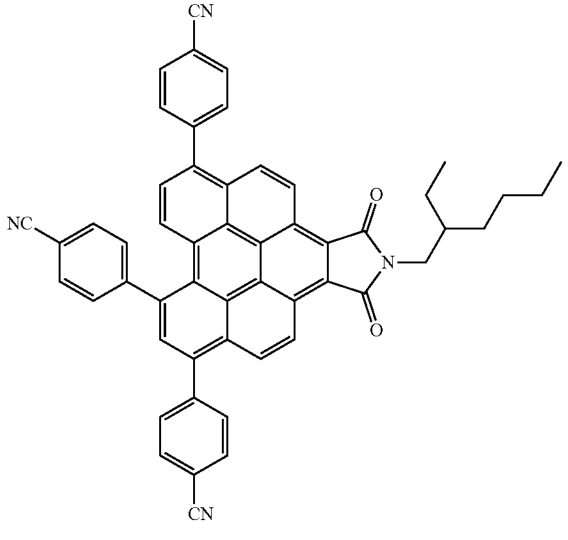

The general procedure above was followed exactly using 4-cyanophenylboronic acid (0.29 g, 6.0 eq.). Yield: 0.23 g, 95%. $^1H$ NMR (300 MHz, Chloroform-d) δ=9.37 (d, J=9.3 Hz, 1H), 9.30 (d, J=9.4 Hz, 1H), 8.31-8.25 (m, 3H), 7.95 (s, 1H), 7.93-7.71 (m, 12H), 7.61 (d, J=8.3 Hz, 1H), 3.73 (d, J=7.2 Hz, 2H), 1.98 (m, 1H), 1.41 (m, 8H), 0.98 (t, J=7.4 Hz, 3H), 0.90 (t, J=6.8 Hz, 3H). $^{13}C$ NMR (75 MHz, Chloroform-d) δ=169.88, 169.82, 149.34, 144.55, 144.28, 138.10, 137.63, 137.11, 133.78, 132.59, 132.44, 131.15, 131.13, 130.13, 129.44, 129.23, 129.13, 129.08, 128.35, 127.52, 127.37, 127.07, 126.51, 124.75, 124.64, 124.49, 124.38, 123.72, 118.60, 118.52, 112.22, 111.98, 111.82, 42.07, 38.60, 30.66, 28.62, 24.02, 23.04, 14.08, 10.53. HRMS (ESI): Calculated for $C_{53}H_{36}N_4O_2$ ([M+]) 760.2833, found 760.2822.

Example 6: Preparation of 2-(2-ethylhexyl)-6,8,11-tris(4-(trifluoromethyl)phenyl)-1H-peryleno[1,12-efg]isoindole-1,3(2H)-dione (4)

4

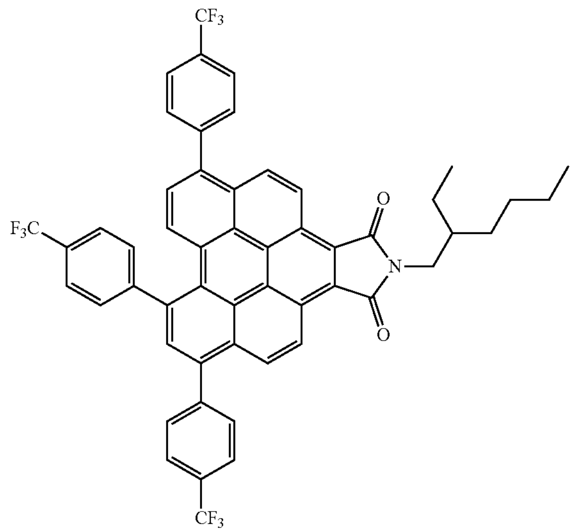

The general procedure above was followed exactly using 4-(trifluoromethyl)phenylboronic acid (0.24 g, 6.0 eq.). The compound was purified by column chromatography using silica as the stationary phase and eluting with 10% hexanes in DCM. It was then recrystallized in DCM/Methanol, the product was filtered and washed sparingly with methanol to give yellow orange solid. Yield: 0.17 g, 60%. $^1H$ NMR (300 MHz, Chloroform-d) δ=9.10 (d, J=9.3 Hz, 1H), 8.97 (d, J=9.3 Hz, 1H), 8.23 (d, J=8.4 Hz, 1H), 8.20 (d, J=9.3 Hz, 1H), 8.14 (d, J=9.3 Hz, 1H), 7.95 (s, 1H), 7.92-7.66 (m, 12H), 7.56 (d, J=8.3 Hz, 1H), 3.58 (d, J=7.3 Hz, 2H), 1.97-1.83 (m, 1H), 1.50-1.27 (m, 8H), 0.96 (t, J=7.4, 3H), 0.89 (t, J=7.0 Hz, 3H). $^{13}C$ NMR (101 MHz, Chloroform-d) δ=169.81, 169.74, 148.61, 143.66, 143.45, 138.36, 138.04, 137.68, 133.35, 130.93, 130.86, 130.62, 130.38, 130.30, 130.06, 129.97, 129.72, 129.36, 129.24, 129.06, 128.93, 128.08, 127.65, 127.57, 127.55, 127.45, 127.32, 127.09, 127.05, 126.82, 126.27, 125.89, 125.86, 125.75, 125.71, 125.70, 124.39, 124.24, 124.19, 124.01, 123.88, 123.15, 122.97, 42.02, 38.71, 30.78, 28.77, 24.12, 23.20, 14.23, 10.66. $^{19}F$ NMR (282 MHz, Chloroform-d) δ=−62.40(3F), −62.43(3F), −62.45(3F). HRMS (ESI): Calculated for $C_{53}H_{36}F_9NO_2$ ([M+]) 775.3298, found 775.3287.

Example 7: Preparation of 2-(2-ethylhexyl)-6,8,11-triphenyl-M-peryleno[1,12-efg]isoindole-1,3(2H)-dione (5)

5

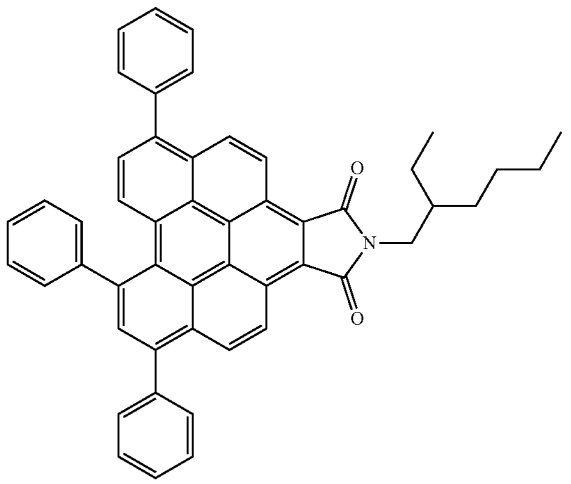

The general procedure was followed exactly using phenylboronic acid (0.24 g, 6.0 eq.). Yield: 0.17 g, 78%. $^1H$ NMR (300 MHz, Chloroform-d) δ=9.16 (d, J=9.3 Hz, 1H), 9.07 (d, J=9.4 Hz, 1H), 8.34 (d, J=9.2 Hz, 1H), 8.31 (d, J=8.1 Hz 1H), 8.29 (d, J=9.4 Hz, 1H), 8.02 (s, 1H), 7.77-7.65 (m, 2H), 7.64-7.36 (m, 14H), 3.68 (d, J=7.2 Hz, 2H), 2.09-1.78 (m, 1H), 1.52-1.21 (m, 8H), 0.98 (t, J=7.4 Hz, 3H), 0.90 (t, J=6.8 Hz, 3H). $^{13}C$ NMR (75 MHz, Chloroform-d) δ=169.89, 169.83, 145.29, 140.30, 140.17, 139.22, 139.07, 139.04, 133.77, 130.68, 130.59, 129.92, 129.25, 129.04, 128.94, 128.74, 128.60, 127.99, 127.88, 127.81, 127.69, 127.61, 127.54, 127.48, 127.45, 127.43, 126.59, 126.08, 124.17, 123.66, 123.57, 123.51, 122.78, 122.28, 41.86, 38.68, 30.80, 28.78, 24.12, 23.21, 14.26, 10.67. HRMS (ESI): Calculated for $C_{50}H_{39}NO_2$ ([M+]) 685.291, found 685.2967.

Example 8: Preparation of 6,8,11-tri([1,1'-biphenyl]-4-yl)-2-(2-ethylhexyl)-1H-peryleno[1,12-efg]isoindole-1,3(2H)-dione (6)

6

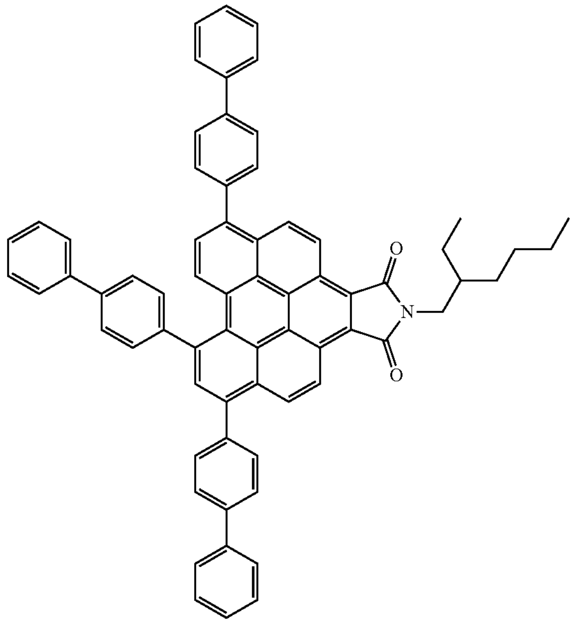

The general procedure above was followed exactly using 4-biphenylboronic acid (0.39 g, 6.0 eq.). Yield: 0.26 g, 89%. $^1$H NMR (400 MHz, Chloroform-d) δ=9.19 (d, J=9.3 Hz, 1H), 9.09 (d, J=9.3 Hz, 1H), 8.44 (d, J=8.4 Hz, 1H), 8.43 (d, J=9.3 Hz, 1H), 8.38 (d, J=9.3 Hz, 1H), 8.11 (s, 1H), 7.89-7.63 (m, 18H), 7.59 (d, J=8.4 Hz, 1H), 7.55-7.46 (m, 6H), 7.46-7.37 (m, 3H), 3.70 (d, J=7.3 Hz, 2H), 2.03-1.93 (m, 1H), 1.50-1.30 (m, 8H), 0.99 (t, J=7.4 Hz, 3H), 0.90 (t, J=7.1 Hz, 3H). $^{13}$C NMR (75 MHz, Chloroform-d) δ=170.30, 170.24, 144.19, 140.81, 140.70, 140.57, 140.38, 139.24, 139.09, 138.88, 138.83, 133.77, 131.14, 131.08, 129.77, 129.25, 129.20, 129.10, 129.06, 128.92, 128.62, 128.30, 128.09, 127.78, 127.68, 127.50, 127.36, 127.34, 127.31, 127.18, 127.03, 126.49, 124.60, 124.13, 124.01, 123.15, 122.67, 42.04, 38.73, 30.81, 28.80, 24.14, 23.24, 14.28, 10.70. HRMS (ESI): Calculated for $C_{68}H_{51}NO_2$ ([M+]) 913.3920, found 913.3920.

Example 9: Preparation of 2-(2-Ethylhexyl)-6,8,11-tris(4-methoxyphenyl)-1H-peryleno[1,12-efg]isoindole-1,3(2H)-dione (7)

7

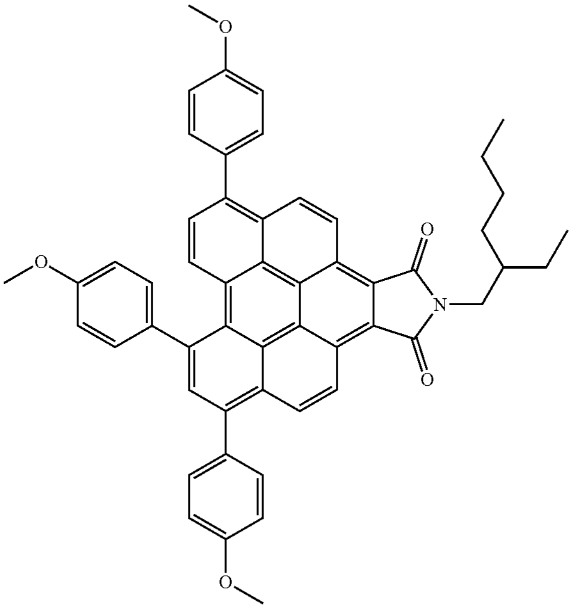

The general procedure above was followed exactly using 4-methoxyphenylboronic acid (0.30 g, 6.0 eq.). Yield: 0.22 g, 89%. $^1$H NMR (300 MHz, Chloroform-d) δ=8.85 (d, J=9.3 Hz, 1H), 8.73 (d, J=9.3 Hz, 1H), 8.21 (d, J=8.4 Hz, 1H), 8.18 (d, J=9.3 Hz, 1H), 8.11 (d, J=9.4 Hz, 1H), 7.90 (s, 1H), 7.56 (d, J=8.6 Hz, 2H), 7.53-7.36 (m, 5H), 7.12 (d, J=8.7 Hz, 2H), 7.09 (d, J=8.6 Hz, 2H), 7.02 (d, J=8.7 Hz, 2H), 3.98 (s, 3H), 3.96 (s, 3H), 3.91 (s, 3H), 3.53 (d, J=7.2, 2H), 1.97-1.82 (m, 1H), 1.50-1.26 (m, 8H), 0.96 (t, J=7.2 Hz, 3H), 0.91 (t, J=6.8 Hz, 3H). $^{13}$C NMR (75 MHz, Chloroform-d) δ=169.92, 169.85, 159.44, 159.30, 159.21, 138.67, 138.64, 138.60, 133.91, 132.68, 132.54, 131.80, 131.72, 130.34, 129.03, 128.85, 128.80, 128.29, 127.97, 127.84, 127.64, 127.46, 127.22, 126.65, 126.11, 124.13, 123.55, 123.34, 123.30, 122.43, 122.03, 115.32, 114.19, 114.08, 55.56, 55.53, 55.53, 55.47, 41.81, 38.68, 30.80, 28.78, 24.12, 23.21, 14.25, 10.66. HRMS (ESI): Calculated for $C_{53}$H45N05 ([M+]) 775.3298, found 775.3287

Example 10: Preparation of 6,8,11-tris(4-(Dimethylamino)phenyl)-2-(2-ethylhexyl)-1H-peryleno[1,12-efg]isoindole-1,3(2H)-dione (8)

8

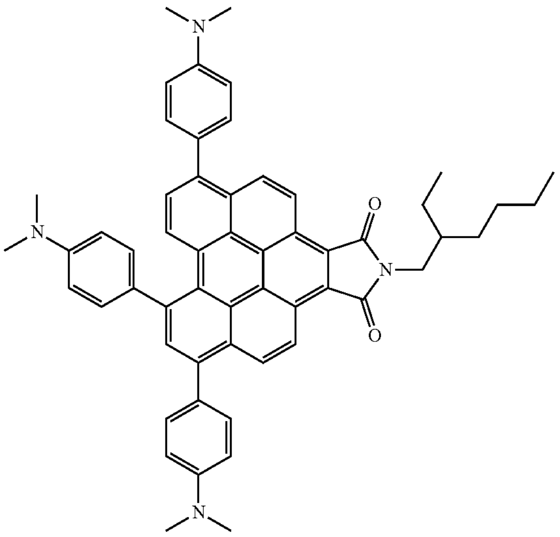

The general procedure above was followed exactly using 4-(dimethylamino)phenylboronic acid (0.43 g, 6.0 eq). Yield: 0.27 g, 77%. $^{1}$H NMR (400 MHz, Chloroform-d) δ=9.25 (d, J=9.3 Hz, 1H), 9.21 (d, J=9.4 Hz, 1H), 8.57 (d, J=8.4 Hz, 1H), 8.53-8.48 (m, 2H), 8.07 (s, 1H), 7.62 (s, 1H), 7.59 (d, J=8.9 Hz, 2H), 7.52 (d, J=8.7 Hz, 2H), 7.48 (d, J=8.7, 2H), 6.93 (dd, J=11.8, 8.3, 4H), 6.87 (d, J=8.2 Hz, 2H), 3.76 (d, J=7.3 Hz, 2H), 3.09 (d, J=6.9 Hz, 12H), 3.05 (s, 6H), 2.01 (m, 1H), 1.58-1.18 (m, 8 Hz), 0.99 (t, J=7.4 Hz, 3H), 0.90 (t, J=7.1 Hz, 3H). $^{13}$C NMR (75 MHz, Chloroform-d) δ=170.70, 170.66, 149.98, 139.23, 133.92, 131.56, 131.52, 130.12, 129.29, 128.83, 128.74, 128.68, 128.54, 128.45, 127.70, 127.35, 127.20, 126.79, 124.83, 124.22, 123.69, 122.29, 122.15, 113.98, 112.79, 42.03, 40.89, 38.75, 30.85, 28.84, 24.18, 23.23, 14.26, 10.71. HRMS (ESI): Calculated for $C_{56}H_{55}N_4O_2$ ([M+]) 815.4320, found 815.4305. Single crystals for SCXRD were grown by slow diffusion of benzene against hexanes.

Example 11: General Procedure for Photoinduced Organocatalyzed Birch Reduction

Into a 1.5-dram scintillation vial was loaded with a Teflon-coated stir bar and photoredox catalyst (1.0 mg, 0.25 mol %). The vial was transferred to an N2 filled glovebox where substrate (0.50 mmol), t-amyl alcohol (0.45 mL, 8.0 eq.), and $N(Me)_4OH$ (2.0 mL, 10 eq. (25% solution in MeOH)) were added. The vial was then sealed using a septum cap, removed from the glovebox, and placed into the light reactor. After 48 hours, the reaction was moved back into the glovebox, where more catalyst (1.0 mg, 0.25 mol %) was added. This was repeated again at 72 hours for a total of 3.0 mg (0.75 mol %) of catalyst added to the reaction. The reaction was stopped at 96 hours and worked up according to the details below.

Example 12: Preparation of 2-(Cyclohexa-1,4-dien-1-yl)ethan-1-ol

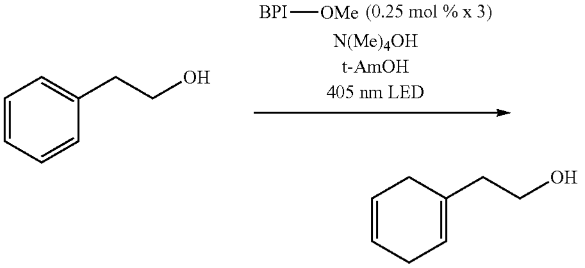

The general procedure was followed using 2-phenyl ethanol. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 43 mg, 70%. $^{1}$H NMR (400 MHz, $CDCl_3$) δ=5.68-5.60 (m, 2H), 5.50-5.46 (m, 1H), 3.63 (t, J=6.27 Hz, 2H), 2.69-2.61 (m, 2H), 2.59-2.51 (m, 2H), 2.21-2.16 (m, 2H) 1.76 (br s, 1H) $^{13}$C NMR (101 MHz, $CDCl_3$) δ=131.4, 124.2, 124.0, 121.4, 60.0, 40.5, 28.7, 26.8.

Example 13: Preparation of 1-Pentylcyclohexa-1,4-diene

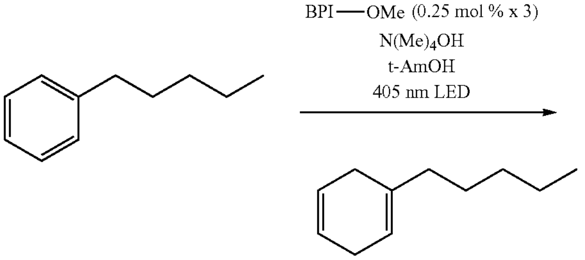

The general procedure was followed using n-pentyl benzene. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 35 mg, 47%. $^{1}$H NMR (400 MHz, $CDCl_3$) δ=5.69-5.59 (m, 2H), 5.36-5.30 (m, 1H), 2.68-2.57 (m, 2H), 2.55-2.48 (m, 2H), 1.94-1.78 (m, 2H), 1.39-1.11 (m, 6H), 0.82, (t, J=7.0 Hz, 3H) $^{13}$C NMR (101 MHz, $CDCl_3$) δ=135.3, 124.4, 124.3, 117.9, 37.5, 31.6, 28.9, 27.0, 26.8, 22.6, 14.1.

Example 14: Preparation of 1-(Cyclohexa-1,4-dien-1-yl)propan-2-ol

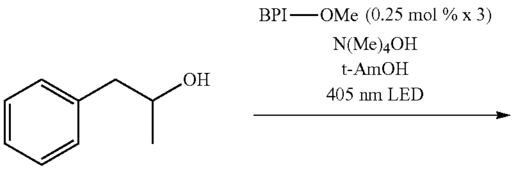

-continued

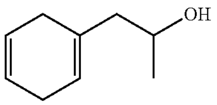

The general procedure was followed using 1-phenyl-2-propanol. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 43 mg, 62%. $^1$H NMR (400 MHz, $CDCl_3$) δ=5.72-5.56 (m, 2H), 5.50-5.40 (m, 1H), 3.84 (dqd, J=8.4 Hz, 6.1 Hz, 4.6 Hz, 1H), 2.71-2.41 (m, 4H), 2.09-1.95 (m, 2H), 1.74 (br s, 1H), 1.13 (d, 6.1 Hz) $^{13}$C NMR (101 MHz, $CDCl_3$) δ=132.1, 124.1, 124.0, 122.1, 64.8, 47.7, 29.0, 26.8, 22.9.

Example 15: Preparation of 1,4-Cyclohexadiene

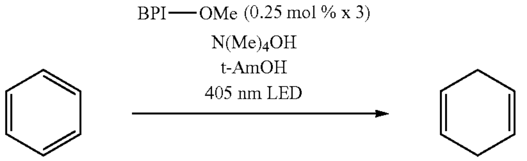

The general procedure was followed using benzene. After the reaction, 1,3,5-trimethoxybenzene (0.1 mmol, 16.8 mg, 0.1 eq.) was added as an internal standard to measure yield by NMR. Yield: 80% (NMR). Because of its volatility, 1,4-cyclohexadiene was not isolated.

Example 16: Preparation of 1-Methylcyclohexa-1,4-diene

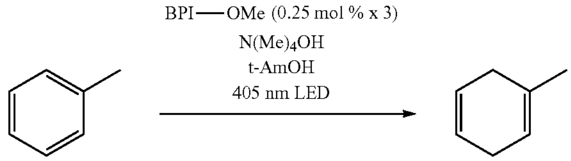

The general procedure was followed using toluene. After the reaction, 1,3,5-trimethoxybenzene (0.1 mmol, 16.8 mg, 0.1 eq.) was added as an internal standard to measure yield by NMR. Yield: 71% (NMR). Because of its volatility, 1-methylcyclohexa-1,4-diene was not isolated.

Example 17: Preparation of (Cyclohexa-1,4-dien-1-ylmethyl)benzene

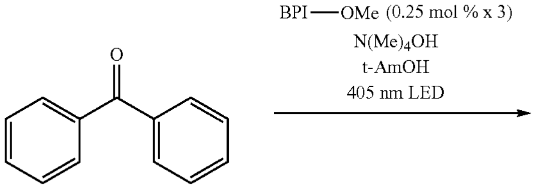

-continued

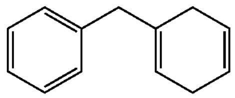

The general procedure was followed using benzophenone. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 36 mg, 42%. $^1$H NMR (400 MHz, $CDCl_3$) δ=7.34-7.27 (m, 2H), 7.25-7.17 (m, 3H), 5.76-5.63 (m, 2H), 5.54-5.47 (m, 1H), 3.34-3.25 (s, 2H), 2.80-2.69 (m, 2H), 2.60-2.49 (m, 2H) $^{13}$C NMR (101 MHz, $CDCl_3$) δ=139.7, 134.5, 129.0, 128.3, 126.0, 124.3, 124.0, 120.3, 44.2, 28.9, 26.9.

Example 18: Preparation of 3-(Cyclohexa-1,4-dien-1-yl)propanoic acid

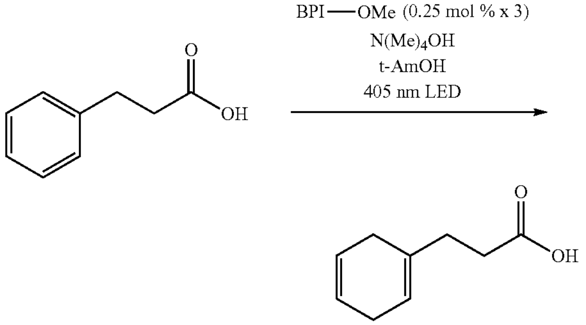

The general procedure was followed using hydrocinnamic acid. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 47 mg, 63%. $^1$H NMR (400 MHz, $CDCl_3$) δ=11.57 (br s, 1H), 5.67-5.58 (m, 2H), 5.42-5.37 (m, 1H), 2.66-2.57 (m, 2H), 2.57-2.49 (m, 2H), 2.47-2.38 (m, 2H), 2.22 (br t, J=7.6 Hz, 2H) $^{13}$C NMR (101 MHz, $CDCl_3$) δ=179.9, 133.0, 124.2, 124.0, 119.2, 32.2, 31.9. 28.9, 26.7.

Example 19: Preparation of Phenylpropan-3-ol

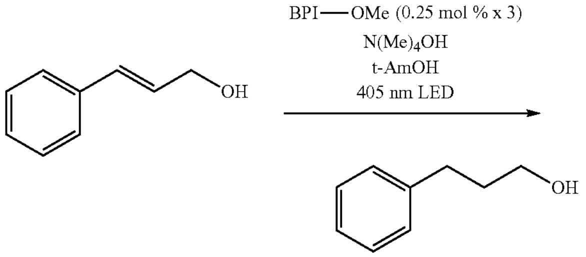

The general procedure was followed using cinnamyl alcohol, except 5.0 eq. of tetramethylammonium hydroxide was used and the reaction was stopped at 24 hours with no further addition of catalyst. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 37 mg, 54%. $^{1}$H NMR (400 MHz, $CDCl_3$) δ=7.34-7.27 (m, 2H), 7.25-7.17 (m, 3H), 3.68 (t, J=6.5 Hz, 2H), 2.72 (br t, J=7.5 Hz, 2H), 1.96-1.86 (m, 2H), 1.74 (br s, 1H) $^{13}$C NMR (101 MHz, $CDCl_3$) δ=141.8, 128.4, 128.4, 125.9, 62.21, 34.2, 32.1.

Example 20: Preparation of 3-(Cyclohexa-1,4-dien-1-yl)propan-1-ol

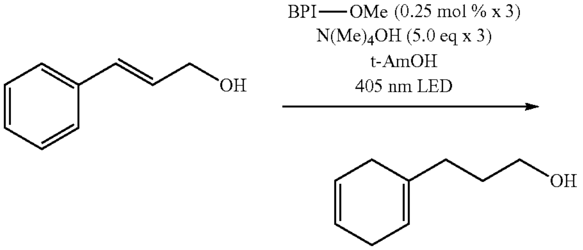

The general procedure was followed using cinnamyl alcohol, except 5.0 eq. of tetramethylammonium hydroxide was used and a further 5.0 eq of tetramethylammonium hydroxide was added with each catalyst addition. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 23 mg, 33%. $^{1}$H NMR (400 MHz, $CDCl_3$) δ=5.76-5.60 (m, 2H), 5.49-5.39 (m, 1H), 3.63 (t, J=6.5 Hz, 2H) 2.72-2.63 (m, 2H), 2.62-2.55 (m, 2H), 2.03 (br t, J=7.6 Hz, 2H), 1.75 (br s, 1H), 1.72-1.64 (m, 2H) $^{13}$C NMR (101 MHz, $CDCl_3$) δ=134.5, 124.3, 124.2, 118.7, 62.7, 33.7, 30.2, 28.9, 26.7.

Example 21: Preparation of 3,4,5,8-Tetrahydro-1H-isochromene

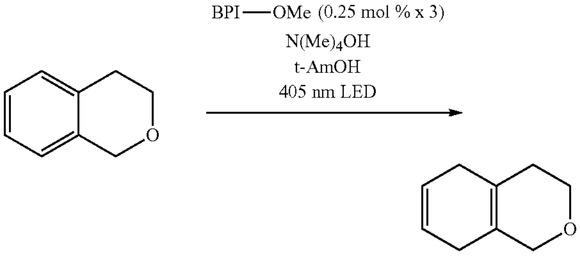

The general procedure was followed using isochroman. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 51 mg, 75%. $^{1}$H NMR (400 MHz, $CDCl_3$) δ=5.78-5.68 (m, 2H), 3.97-3.90 (m, 2H), 3.83 (t, J=5.57 Hz, 2H), 2.64-2.52 (m, 2H), 2.51-2.40 (m, 2H), 2.05-1.94 (m, 2H) $^{13}$C NMR (101 MHz, $CDCl_3$) δ=124.9, 124.3, 123.6, 123.6, 68.1, 64.9, 30.7, 29.1, 26.5.

Example 22: Preparation of 4-Phenylbutanoic acid

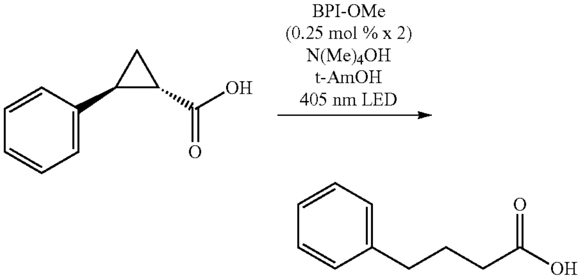

The general procedure was followed using 2-phenylcyclopropane-1-carboxylic acid, except catalyst was only added one time and the reaction was stopped after 72 hours. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 59 mg, 73%. $^{1}$H NMR (400 MHz, $CDCl_3$) δ=11.51 (br, s), 7.33-7.27 (m, 2H), 7.24-7.16 (m, 3H), 2.69 (t, J=7.43 Hz, 2H), 2.39 (t, J=7.42 Hz, 2H), 1.98 (dt, J=7.61, 7.00 Hz, 2H) $^{13}$C NMR (101 MHz, $CDCl_3$) δ=180.0, 141.2, 128.5, 128.4, 126.1, 35.0, 33.3, 26.2.

Example 23: Preparation of 4-(Cyclohexa-1,4-dien-1-yl)butanoic acid

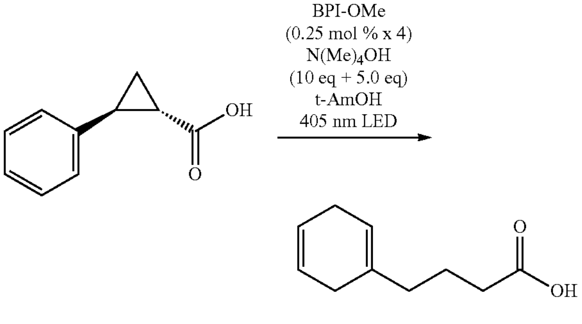

The general procedure was followed using 2-phenylcyclopropane-1-carboxylic acid, except catalyst was added once more after 96 hours along with another 1 mL of TMAOH solution and the reaction was stopped after 144 hours. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 33 mg, 40%. $^{1}$H NMR (400 MHz, $CDCl_3$) δ=11.56 (br s, 1H), 5.75-5.64 (m, 2H), 5.46-5.39 (m, 1H), 2.73-2.63 (m, 2H), 2.62-2.54 (m, 2H), 2.35 (t, J=7.45 Hz, 2H), 2.02 (br t, J=7.52 Hz, 2H), 1.77 (dt, J=7.65, 7.39 Hz, 2H) $^{13}$C NMR (101 MHz, $CDCl_3$) δ=180.4, 133.7, 124.2, 124.2, 119.4, 36.6, 33.5, 28.7, 26.7, 22.2.

Example 24: Preparation of t-Butyl phenylethyl carbamate

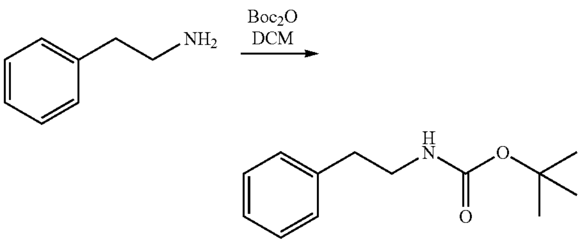

2-Phenylethylamine (3.0 g, 0.025 mol, 1 eq.) was added to a solution of $Boc_2O$ (6.0 g, 0.028 mol, 1.1 eq.) in DCM (20 mL). This solution was stirred for 2 hours and then concentrated by rotary evaporation. The resulting solid was purified by recrystallization from DCM:hexanes. The solid was collected by vacuum filtration and further purified by flash chromatography (silica, 40 g, gradient of 15% ethyl acetate in hexanes) resulting in the desired product as a white solid that was dried under vacuum overnight. Yield (3.3 g, 60%)$^1$H NMR (400 MHz, $CDCl_3$) δ=7.34-7.28 (m, 2H, 7.25-7.16 (m, 3H), 4.53 (br s, 1H), 3.45-3.29 (m, 2H), 2.80 (t, J=7.02 Hz, 2H), 1.44 (s, 9H). $^{13}$C NMR (101 MHz, $CDCl_3$) δ=155.9, 139.0, 128.8, 128.6, 126.4, 79.2, 41.8, 36.2, 28.4.

Example 25: Preparation of tert-butyl (2-(cyclohexa-1,4-dien-1-yl)ethyl)carbamate

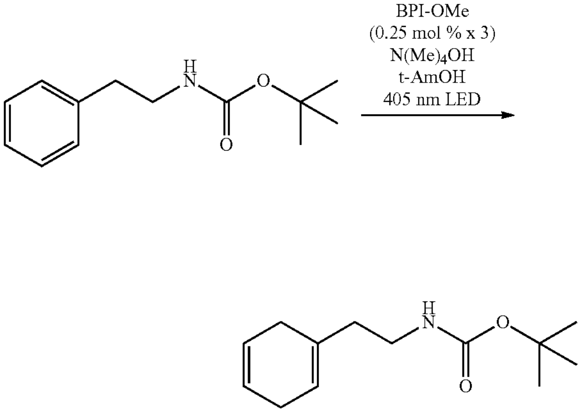

The general procedure was followed using t-butyl phenylethyl carbamate. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 11 mg, 32%. $^1$H NMR (400 MHz, $CDCl_3$) δ=5.65-5.61 (m, 2H), 5.44-5.39 (m, 1H), 4.43 (br s, 1H), 3.15 (br t, J=6.68 Hz, 2H), 2.68-2.59 (m, 2H), 2.57-2.48 (m, 2H), 2.08 (br t, J=6.67 Hz, 2H), 1.37 (s, 9H) $^{13}$C NMR (101 MHz, $CDCl_3$) δ=155.9, 131.8, 124.1, 124.0, 120.8, 79.1, 38.1, 37.6, 28.6, 28.4, 26.7.

Example 26: Preparation of 2-(5-Methylcyclohexa-1,4-dien-1-yl)ethan-1-ol

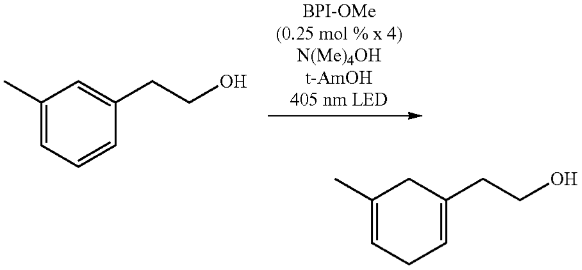

The general procedure was followed using 2-(3-methylphenyl)ethanol, except catalyst was added once more after 96 hours along with another 1 mL of TMAOH solution and the reaction was stopped after 144 hours. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 35 mg, 51%. $^1$H NMR (400 MHz, $CDCl_3$) δ=5.55-5.49 (m, 1H), 5.41-5.36 (m, 1H), 3.68 (t, J=6.34 Hz, 2H), 2.73-2.63 (m, 2H), 2.53-2.45 (m, 2H), 2.24 (t, J=6.18 Hz, 2H), 1.78 (s, 1H), 1.66 (s, 3H) $^{13}$C NMR (101 MHz, $CDCl_3$) δ=131.3, 131.0, 121.3, 118.4, 60.0, 40.3, 33.7, 27.7, 23.1.

Example 27: Preparation of 1,2,3,4,5,8-Hexahydronaphthalene

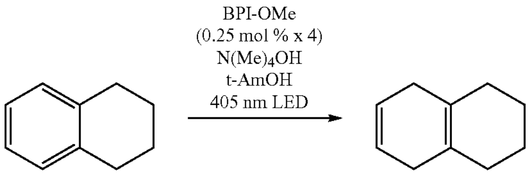 [SMILES: c1ccc2c(c1)CCCC2 ; C1=CCC2=C(C1)CCCC2]

The general procedure was followed using 1,2,3,4-tetrahydronaphthalene, except catalyst was added once more after 96 hours along with another 1 mL of TMAOH solution and the reaction was stopped after 144 hours. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 26 mg, 38%. $^1$H NMR (400 MHz, $CDCl_3$) δ=5.75-5.69 (m, 2H), 2.53 (app s, 4H), 1.92-1.82 (m, 2H), 1.69-1.60 (m, 2H) $^{13}$C NMR (101 MHz, $CDCl_3$) δ=125.6, 124.6, 31.6, 29.8, 23.2

Example 28: Preparation of methyl (2-(5-Methylcyclohexa-1,4-dien-1-yl)ethyl)carbamate

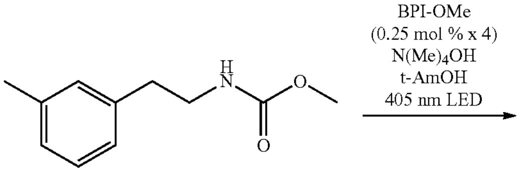

-continued

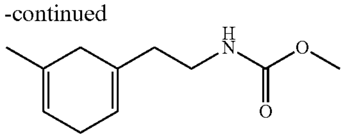

The general procedure was followed using methyl (3-methylphenethyl)carbamate, except catalyst was added once more after 96 hours along with another 1 mL of TMAOH solution and the reaction was stopped after 144 hours. After the reaction, volatiles were removed using a rotary evaporator and the residue was flashed through a plug of silica. The eluent was then concentrated and purified via flash column chromatography (Silica, gradient of 0-30% EtOAc in Hexanes) resulting in a colorless oil. Yield: 47 mg, 48%. $^{1}$H NMR (400 MHz, $CDCl_3$) δ=5.50-5.45 (m, 1H), 5.42-5.36 (m, 1H), 4.83-4.44 (m, 1H), 3.73-3.59 (m, 3H), 3.34-3.16 (m, 2H), 2.72-2.62 (m, 2H), 2.51-2.42 (m, 2H), 2.22-2.12 (m, 2H), 1.67 (s, 3H) $^{13}$C NMR (101 MHz, $CDCl_3$) δ=156.9, 131.6, 130.9, 120.8, 118.4, 52.0, 38.4, 37.2, 33.5, 27.7, 23.1.

Example 29: Preparation of methyl 3,4,5,8-tetrahydroisoquinoline-2(1H)-carboxylate

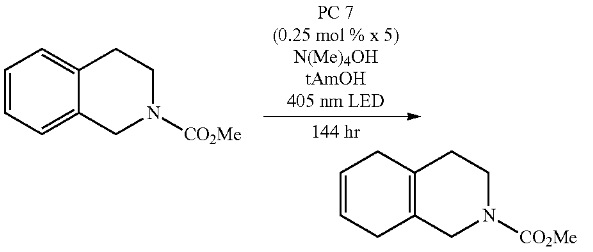

The general procedure was followed using methyl 3,4-dihydroisoquinoline-2(1H)-carboxylate. After the reaction, volatiles were removed using a rotary evaporator and the residue was flashed through a plug of silica. The eluent was then concentrated and purified by silica gel flash column chromatography (gradient of 0-10% EtOAc in Hexanes) resulting in a colorless oil. Yield: 38.4 mg, 40%. 1H NMR (400 MHz, $CDCl_3$) δ=5.79-5.65 (m, 2H), 3.82-3.65 (m, 5H), 3.63-3.48 (m, 2H), 2.62-2.47 (m, 4H), 2.05-1.94 (m, 2H). 13C NMR (101 MHz, $CDCl_3$) δ=156.0, 126.5, 126.3, 124.1, 123.6, 52.5, 46.3, 40.7, 30.9, 29.1, 28.3. DART: Calcd. for $C_{11}H_{16}NO_2$ [M+H]+ 194.1181, found 194.1181.

Example 30: Preparation of (cyclohexa-1,4-dien-1-yloxy)benzene, (cyclohex-1-en yloxy)benzene, 1,1'-oxydicyclohexa-1,4-diene, and 1-(cyclohex-1-en-1-yloxy)cyclohexa-1,4-diene

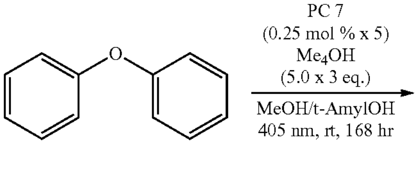

-continued

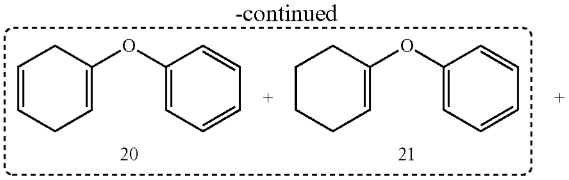

20 21

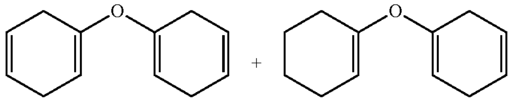

22 23

The general procedure was followed using diphenyl ether, except catalyst was added 6 times at 24 hr intervals and 5.0 eq. of Me4NOH was used and a further 5.0 eq. of Me4NOH was added at 48 hr intervals. After the reaction, volatiles were removed using a rotary evaporator and the residue was flashed through a plug of silica. The eluent was then concentrated and purified by silica gel flash column chromatography (gradient of 0-2% EtOAc in Hexanes) resulting in colorless oils. Because of the small differences in the Rf the products were collected as two fractions, each being a mixture of two compounds in the ratios listed.

Fraction 1: a 5.6:1 mixture of (cyclohexa-1,4-dien-1-yloxy)benzene (20) and (cyclohex-1-en-1-yloxy)benzene (21) Yield: 32.1 mg, 37%.

(cyclohexa-1,4-dien-1-yloxy)benzene (20): 1H NMR (400 MHz, CDCl3) ö=7.39-7.24 (m, 2H), 7.11-6.97 (m, 3H), 5.77-5.67 (m, 2H), 5.03-4.98 (m, 1.00H), 2.96-2.75 (m, 4H). 13C NMR (101 MHz, CDCl3) ö=155.8, 150.9, 129.5, 124.3, 123.2, 123.0, 119.2, 103.4, 27.6, 26.6. DART: Calcd. for C12H130 [M+H]+ 173.0966, found 173.0965.

(cyclohex-1-en-1-yloxy)benzene (21): 1H NMR (400 MHz, CDCl3) ö=7.39-7.24 (m, 0.36H), 7.11-6.97 (m, 0.54H), 5.11-5.04 (m, 0.18H), 2.24-2.15 (m, 0.36H), 2.13-2.04 (m, 0.36H), 1.82-1.71 (m, 0.36H), 1.67-1.57 (m, 0.36H). 13C NMR (101 MHz, CDCl3) ö=156.3, 153.1, 129.4, 122.5, 118.7, 107.1, 26.6, 23.6, 22.9, 22.3. DART: Calcd. for C12H130 [M+H]+ 173.0966, found 173.0965. DART: Calcd. for C12H150 [M+H]+ 175.1123, found 175.1122.

Fraction 2: a 8.3:1 mixture of 1,1'-oxydicyclohexa-1,4-diene (22) and 1-(cyclohex-1-en-1-yloxy)cyclohexa-1,4-diene (23) (8.3:1) Yield: 11.8 mg, 14%.

1,1'-oxydicyclohexa-1,4-diene (22): 1H NMR (400 MHz, $CDCl_3$) ö=5.77-5.60 (m, 4H), 5.13-5.03 (m, 2H), 2.88-2.70 (m, 8H). 13C NMR (101 MHz, $CDCl_3$) ö=148.7, 124.2, 123.3, 103.0, 27.2, 26.6. DART: Calcd. for C12H150 [M+H]+ 175.1123, found 175.1123.

1-(cyclohex-1-en-1-yloxy)cyclohexa-1,4-diene (23): 1H NMR (400 MHz, CDCl3) ö=5.77-5.60 (m, 0.48H), 5.13-5.03 (m, 0.24H), 5.03-4.95 (m, 0.24H), 2.88-2.70 (m, 0.96H), 2.13-2.01 (m, 0.96H), 2.75-2.64 (m, 0.48H), 1.63-1.52 (m, 0.48H). 13C NMR (101 MHz, CDCl3) ö=151.1, 149.2, 124.3, 123.4, 106.7, 101.7, 29.7, 27.4, 26.3, 23.7, 22.9, 22.3. DART: Calcd. for C12H170 [M+H]+177.1279, found 177.1282.

Example 31: Preparation of (cyclohexa-1,4-dien-1-ylmethyl)benzene

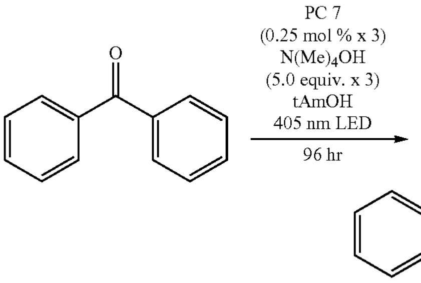

25

The general procedure was followed using benzophenone, except both PC (0.25 mol %) and Me4NOH (5.0 eq.) were added at 24 hr intervals. After the reaction, volatiles were removed using a rotary evaporator and the residue was flashed through a plug of silica. The eluent was then concentrated and purified by silica gel flash column chromatography (hexanes) resulting in a colorless oil. Yield: 36.0 mg, 42%. $^{1}$H NMR (400 MHz, $CDCl_3$) δ=7.34-7.27 (m, 2H), 7.25-7.17 (m, 3H), 5.76-5.63 (m, 2H), 5.54-5.47 (m, 1H), 3.34-3.25 (s, 2H), 2.80-2.69 (m, 2H), 2.60-2.49 (m, 2H) $^{13}$C NMR (101 MHz, $CDCl_3$) δ=139.7, 134.5, 129.0, 128.3, 126.0, 124.3, 124.0, 120.3, 44.2, 28.9, 26.9. DART: Calcd. for $C_{13}H_{15}$ $[M+H]^+$ 171.1174, found 171.1178.

Example 32: Preparation of phenylpropan-3-ol

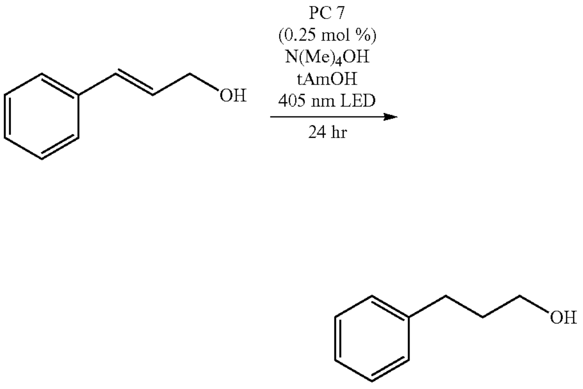

27

The general procedure was followed using cinnamyl alcohol, except 5.0 eq. of Me4NOH was used and the reaction was stopped at 24 hours with no further addition of catalyst. After the reaction, volatiles were removed using a rotary evaporator and the residue was flashed through a plug of silica. The eluent was then concentrated and purified by silica gel flash column chromatography (gradient of 0-10% EtOAc in Hexanes) resulting in a colorless oil. Yield: 36.6 mg, 54%. $^{1}$H NMR (400 MHz, $CDCl_3$) δ=7.34-7.27 (m, 2H), 7.25-7.17 (m, 3H), 3.68 (t, J=6.5 Hz, 2H), 2.72 (br t, J=7.5 Hz, 2H), 1.96-1.86 (m, 2H), 1.74 (br s, 1H) $^{13}$C NMR (101 MHz, $CDCl_3$) δ=141.8, 128.4, 128.4, 125.9, 62.21, 34.2, 32.1.

Example 33: Preparation of 3-(cyclohexa-1,4-dien-1-yl)propan-1-ol

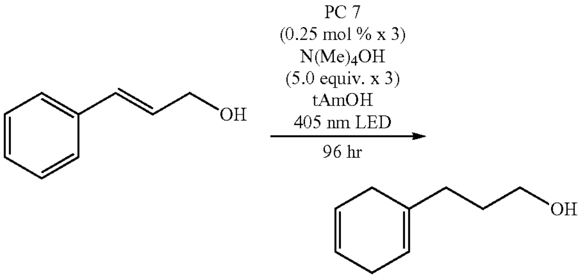

28

The general procedure was followed using cinnamyl alcohol, except 5.0 eq. of Me4NOH was used and a further 5.0 eq. of Me4NOH was added with each catalyst addition. After the reaction, volatiles were removed using a rotary evaporator and the residue was flashed through a plug of silica. The eluent was then concentrated and purified by silica gel flash column chromatography (gradient of 0-10% EtOAc in Hexanes) resulting in a colorless oil. Yield: 22.7 mg, 33%. $^{1}$H NMR (400 MHz, $CDCl_3$) δ=5.76-5.60 (m, 2H), 5.49-5.39 (m, 1H), 3.63 (t, J=6.5 Hz, 2H) 2.72-2.63 (m, 2H), 2.62-2.55 (m, 2H), 2.03 (br t, J=7.6 Hz, 2H), 1.75 (br s, 1H), 1.72-1.64 (m, 2H) 13C NMR (101 MHz, CDCl3) δ=134.5, 124.3, 124.2, 118.7, 62.7, 33.7, 30.2, 28.9, 26.7. DART: Calcd. for C9H15O $[M+H]^+$ 139.1123, found 139.1122.

Example 34: Preparation of 4-phenylbutanoic acid

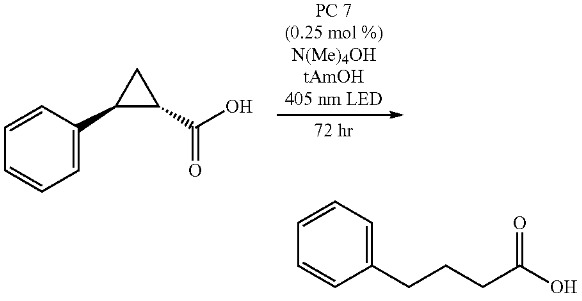

30

The general procedure was followed using 2-phenylcyclopropane-1-carboxylic acid, except catalyst was only added one time at 48 hr and the reaction was stopped after 72 hr. After the reaction, volatiles were removed using a rotary evaporator and the residue was flashed through a plug of silica. The eluent was then concentrated and purified by silica gel flash column chromatography (gradient of 0-10% EtOAc in Hexanes) resulting in a white solid. Yield: 59 mg, 73%. $^{1}$H NMR (400 MHz, CDCl3) δ=11.51 (br, s), 7.33-7.27 (m, 2H), 7.24-7.16 (m, 3H), 2.69 (t, J=7.43 Hz, 2H), 2.39 (t, J=7.42 Hz, 2H), 1.98 (dt, J=7.61, 7.00 Hz, 2H) $^{13}$C NMR (101 MHz, CDCl3) δ=180.0, 141.2, 128.5, 128.4, 126.1, 35.0, 33.3, 26.2.

Example 35: Preparation of 4-(cyclohexa-1,4-dien-1-yl)butanoic acid

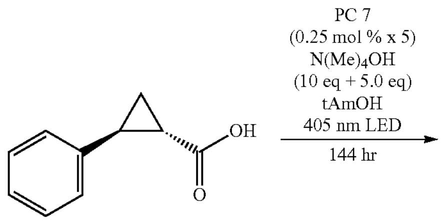

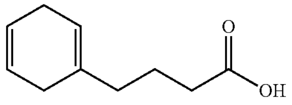

31

The general procedure was followed using 2-phenylcyclopropane-1-carboxylic acid, except catalyst was added once more after 96 hours along with another 1 mL of TMAOH solution and the reaction was stopped after 144 hours. After the reaction, volatiles were removed using a rotary evaporator and the residue was flashed through a plug of silica. The eluent was then concentrated and purified by silica gel flash column chromatography (gradient of 0-10% EtOAc in Hexanes) resulting in a white solid. Yield: 33.1 mg, 40%. $^{1}H$ NMR (400 MHz, CDCl3) δ=11.56 (br s, 1H), 5.75-5.64 (m, 2H), 5.46-5.39 (m, 1H), 2.73-2.63 (m, 2H), 2.62-2.54 (m, 2H), 2.35 (t, J=7.45 Hz, 2H), 2.02 (br t, J=7.52 Hz, 2H), 1.77 (dt, J=7.65, 7.39 Hz, 2H) $^{13}C$ NMR (101 MHz, CDCl3) δ=180.4, 133.7, 124.2, 124.2, 119.4, 36.6, 33.5, 28.7, 26.7, 22.2. DART: Calcd. for C10H1502 $[M+H]^+$ 167.1072, found 167.1071.

Example 36: Preparation of Ethyl 4-(5,6-dihydro-11H-benzo[5,6]cyclohepta[1,2-b]pyridin-11-ylidene) piperidine-1-carboxylate and Methyl 4-(5,6-dihydro-11H-benzo[5,6]cyclohepta[1,2-b]pyridin-11-ylidene)piperidine-1-carboxylate

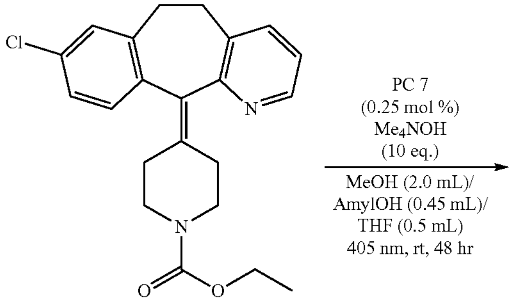

-continued

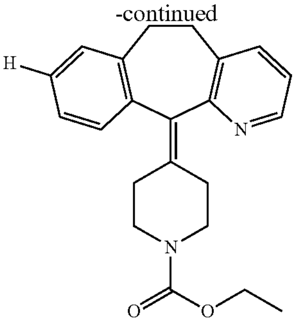

+

33

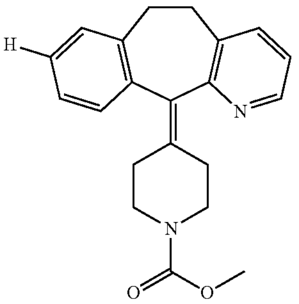

34

The general procedure was followed using loratadine except the reaction was stopped at 48 hr and not further catalyst was added. After the reaction, volatiles were removed using a rotary evaporator and the residue was flashed through a plug of silica. The eluent was then concentrated and purified by silica gel flash column chromatography (gradient of 10-30% EtOAc in Hexanes) resulting in white solids.

Ethyl 4-(5,6-dihydro-11H-benzo[5,6] cyclohepta[1,2-b]pyridin-11-ylidene)piperidine-1-carboxylate (33)

Yield: 112.7 mg, 65%. 1H NMR (400 MHz, $CDCl_3$) δ=8.42-8.34 (m, 1H), 7.46-7.37 (m, 1H), 7.23-7.10 (m, 4H), 7.10-7.01 (m, 1H), 4.12 (q, J=7.10 Hz, 2H), 3.91-3.72 (m, 2H), 3.48-3.28 (m, 2H), 3.19-3.07 (m, 2H), 2.90-2.74 (m, 2H), 2.55-2.25 (m, 4H), 1.24 (t, J=7.10 Hz, 3H). 13C NMR (101 MHz, CDCl3) δ=157.3, 155.5, 146.4, 139.3, 137.7, 137.6, 136.8, 135.2, 133.7, 129.2, 129.0, 127.4, 126.0, 122.1, 61.3, 44.9, 44.8, 31.8, 31.8, 30.7, 30.5, 14.7. DART: Calcd. for C22H25N2O2 [M+H]+ 349.1916, found 349.1917.

Methyl 4-(5,6-dihydro-11H-benzo[5,6] cyclohepta [1,2-b]pyridin-11-ylidene)piperidine-1-carboxylate (34)

Yield: 44.0 mg, 26%. 1H NMR (400 MHz, CDCl3) δ=8.46-8.31 (m, 1H), 7.50-7.36 (m, 1H), 7.22-7.04 (m, 5H), 3.92-3.72 (m, 2H), 3.68 (s, 3H), 3.48-3.29 (m, 2H), 3.16-3.09 (m, 2H), 2.90-2.75 (m, 2H), 2.55-2.24 (m, 4H). 13C NMR (101 MHz, CDCl3) δ=157.1, 155.9, 146.2, 139.2, 137.9, 137.6, 136.9, 135.0, 133.8, 129.2, 129.0, 127.5, 126.1, 122.2, 52.6, 44.9, 44.9, 31.8, 31.7, 30.7, 30.5. DART: Calcd. for C21H23N2O2 [M+H]+ 335.1760, found 335.1757.

Example 37: Functional Group Capability and Selectivity

Again, with reference to FIG. 3A-3D, the generality of a photoinduced organocatalyzed Birch reduction (O-PBR)

using substrates with varied functional groups was explored. The results of these reductions are shown in FIG. 4A-4B. With reference to FIG. 4A, alcohols and carboxylic acids containing were well tolerated, affording 1,4-cyclohexadiene products 10-12 and 17 in 51-72% conversions. The reduction of the alkyl-functionalized arene pentylbenzene proceeded well, resulting in 13 in 47% conversion. Importantly, the Birch reduction of benzene and toluene were high-yielding, with 80% and 71% conversion by $^1$H NMR, respectively. Interesting reactivity was identified using the optimized conditions, such as the stepwise deoxygenation/Birch reduction of benzophenone which provided 1-benzyl-1,4-cyclohexadiene 16 in 42% conversion. Isochroman subjected to the O-PBR protocol afforded product 21 in 75% conversion. This is an interesting result, because C—O bond cleavage dominates in a lithium-based Birch reduction.[11]

With reference to FIG. 4B, selective reductions can be accomplished with molecules containing multiple reactive functional groups. By manipulating the amount of Me4NOH and reaction time, cinnamyl alcohol gave either phenylpropanol 23 or the Birch reduction product 24 in 54% and 33% conversion, respectively. Similarly, the reaction of 25 underwent a reductive ring-opening process to give 26 in 73% conversion, while further reduction provided 1,4-cyclohexadienyl product 27 in 40% conversion.

anion then absorbs the second photon to produce excited state 7d. This excited state species then reduces the substrate via photoinduced electron transfer (PET), forming the substrate radical anion and reforming the ground state PC 7a. The radical anion of the substrate is then protonated by the alcohol to form a neutral radical. A second complete catalytic cycle results in reduction of the neutral radical to a closed-shell anion, which upon protonation gives the product.[7]

Example 38: Optimization of Sacrificial Electron Donor

BPI's ConPET reactivity was investigated by developing an O-PBR. Trialkylamines have been employed as the sacrificial electron donor in most reports of ConPET, but in accordance with the present disclosure it was found that they were not reducing enough to work with BPIs. As such, $F^-$ and $OH^-$ were utilized, which are both powerful reductants and strong bases. While both of these anions worked in O-PBR, $OH^-$ outperformed $F^-$ so this anion was chosen for the next step of optimization.

TABLE 1

Optimization of Photoredox Birch Reduction of Phenylethanol[a]

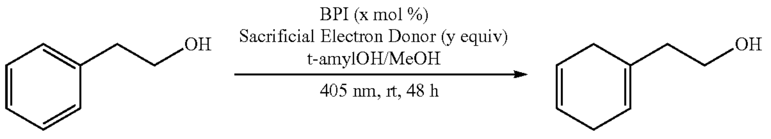

9 10

| Entry | BPI | x | Sacrificial Electron Donor | y | Time (hr) | Conv. %[b] |
|---|---|---|---|---|---|---|
| 1 | 1 | 0.25 | $Bu_4NOH$ | 2.0 | 16 | 3 |
| 2 | 3 | 0.25 | $Bu_4NOH$ | 2.0 | 16 | 5 |
| 3 | 4 | 0.25 | $Bu_4NOH$ | 2.0 | 16 | 8 |
| 4 | 5 | 0.25 | $Bu_4NOH$ | 2.0 | 16 | 12 |
| 5 | 6 | 0.25 | $Bu_4NOH$ | 2.0 | 16 | 2 |
| 6 | 7 | 0.25 | $Bu_4NOH$ | 2.0 | 16 | 17 |
| 7 | 8 | 0.25 | $Bu_4NOH$ | 2.0 | 16 | 3 |
| 8 | 7 | 0.25 | $Et_4NOH$ | 2.0 | 16 | 9 |
| 9 | 7 | 0.25 | $Me_4NOH$ | 2.0 | 16 | 25 |
| 10 | 7 | 0.25 | $Hex_4NOH$ | 2.0 | 16 | 1 |
| 11 | 7 | 0.25 | $Me_4NOH$ | 5.0 | 48 | 33 |
| 12 | 7 | 0.25 | $Me_4NOH$ | 10.0 | 48 | 42 |
| 13 | 7 | 0.10 | $Me_4NOH$ | 10.0 | 48 | 20 |
| 14 | 7 | 0.50 | $Me_4NOH$ | 10.0 | 48 | 43 |
| 15 | 7 | 1.0 | $Me_4NOH$ | 10.0 | 48 | 33 |
| 16 | 7 | 0.25 x 3[c] | $Me_4NOH$ | 10.0 | 96 | 88 (70[d]) |

[a]Conditions: A mixture of BPI, 9 (0.50 mmol), sacrificial electron source, and solvent were irradiated with 405 nm LEDs for indicated time at room temperature.
[b]Determined by crude $^1$H NMR.
[c]BPI was added in three portions at t = 0 hr, 48 hr, and 72 hr.
[d]Isolated conversion.

Figures 5A, 5B, 5C, 5D:
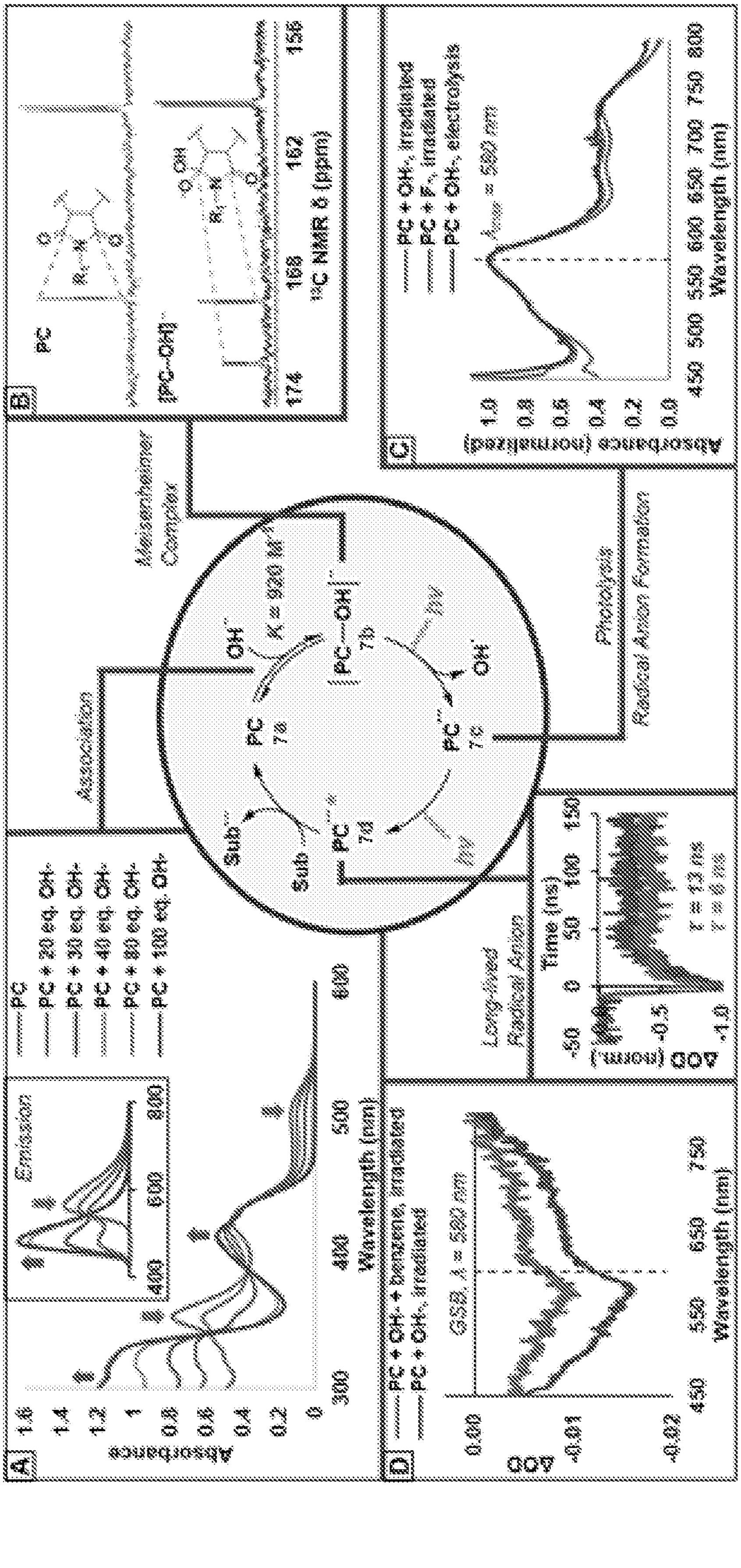
FIG. 5A-5D. Mechanistic studies of photocatalyzed Birch reduction. (A) UV-visible spectra of increasing molar ratios of hydroxide:BPI 7a from 0:1-100:1, 0.02 mM in BPI in THF. Inset: emission spectra of the same mixtures at $\lambda_{excitation}$=416 nm. (B)$^{13}C$ NMR spectra of 7a and a 100:1 ratio of hydroxide:7a in deuterated THF. (C) Normalized absorbance spectra of 7a (0.2 mM in THF)+10 eq. hydroxide after 1 min irradiation at 405 nm, 7a (0.2 mM in THF)+200 eq. fluoride after 10 s irradiation at 405 nm, and 7a (0.02 mM in THF)+100 eq. hydroxide after 7 min electrolysis at $E_{app}$=—2.6 V vs. Ag/$AgNO_3$. (D) Left: spectral absorption trace at $\lambda_{pump}$=532 nm of a mixture of 7a (0.2 mM in THF)+10 eq. hydroxide with (red traces) and without (blue traces) 100 eq. benzene, pre-irradiated with 405 nm light for 1 min. Right: time-resolved kinetic traces with $\lambda_{pump}$=532 nm and $\lambda_{probe}$=580 nm of the same mixtures. K=equilibrium constant for hydroxide association. Sub=substrate. PC=photocatalyst. Hydroxide source was anhydrous tetrabutylammonium hydroxide solution (1M in MeOH).

With reference to FIG. 5A-5D, mechanistically, in accordance with aspects of the disclosure and without intending to be limited, investigations showed a catalytic cycle utilizing 2 photons per turnover and 4 photons per mole of product formed (FIG. 5A). Prior to light absorption, the imide moiety of PC 7a is attacked by the nucleophilic hydroxide to form the Meisenheimer complex 7b. Next, the anionic Meisenheimer complex undergoes photoinduced homolytic cleavage of the C—OH bond to produce radical anion 7c and a hydroxy radical. We propose that this radical With reference to Table 1 above and FIG. 3A-3D, once reactivity was established, a suite of benzo[ghi]perylene monoimide (BPI) derivatives in the reduction of 2-phenylethanol (9) was investigated. The reactions contained 2.0 equivalents of $Bu_4NOH$ as the sacrificial electron donor, in mixed MeOH and tert-amyl alcohol (t-AmylOH), and used 405 nm LED irradiation (Table 1, entries 1-7).

The results of this comparison of photocatalysts (PCs) 1 and 3-8 showed that 7 is the most efficient BPI derivative for O-PBR, achieving 17% conversion to the Birch reduction product 10 in 16 hr (entry 5). Systematically screening the counter-cations and counter-anions of potential sacrificial electron sources revealed that the smaller cation, Me4NOH, increased the conversion to 25% (entry 9). Increasing the loading of Me4NOH to 10 equivalents and the reaction time to 48 hr lead to higher conversions (entries 11-12). Importantly, lower PC loading (0.10 mol %) is still able to drive the reactivity (entry 13). Increased PC loading did not increase the conversion (entries 14-15), possibly due unproductive interactions between the ground and excited states of BPI 7. We found that adding 0.75 mol % of 7 in three portions was optimal, achieving 88% conversion in 96 hours (entry 16). Control experiments revealed that the light source significantly impacts the conversion, and no reactivity was observed in the absence of either light or Me4NOH.

Example 39: Optimization of Conditions for Birch Reduction

Using the general procedure described above (Example 11), the catalyst choice and light source were optimized. The specific photoredox catalysts are described above and the substrate is 2-phenylethanol. Table 1 and Table 2, shown below, shows the results.

TABLE 2

Optimization of Photoredox Catalyst

| Conditions: | | | |
|---|---|---|---|
| Catalyst | 1.0 mg | 0.001 mmol | 0.25 mol % |
| PhEtOH | 0.06 mL | 0.5 mmol | 1 eq |
| TMAOH/MeOH | 1.0 mL | 1.0 mmol | 2 eq |
| tAmOH | 0.9 mL | 8.0 mmol | 16 eq |
| | Light at 405 nm. | | |

| Catalyst | Conv. @ 20 hr |
|---|---|
| BPI 1 | 3% |
| BPI 3 | 5% |
| BPI 4 | 8% |
| BPI 5 | 12% |
| BPI 6 | 2% |
| BPI 7 | 17% |
| BPI 8 | 3% |

TABLE 3

Light Source Optimization

| Conditions: | | | |
|---|---|---|---|
| BPI 7 | 1.0 mg | 0.001 mmol | 0.25 mol % |
| PhEtOH | 0.06 mL | 0.5 mmol | 1 eq |
| TMAOH/MeOH | 1.0 mL | 1.0 mmol | 2 eq |
| tAmOH | 0.45 mL | 4.0 mmol | 8 eq |

| Lights | Conv. @ 20 hr |
|---|---|
| 365 nm | 14% |
| 395 nm | 20% |
| 405 nm | 20% |
| 457 nm | 8% |
| Cool White | 2% |
| 523 nm | 0% |
| 590 nm | 0% |
| 740 nm | 0% |

Example 40: Mechanistic Experiments

Mechanistic experiments focused on identifying the role of the hydroxide additive in the method. In related work exploring interactions between hydroxide and PDIs or naphthalene diimides (NDIs), hydroxide was observed to perform thermally-induced single electron transfer (SET) to generate the radical anion of the PDI or NDI and a hydroxy radical.[12,13] With BPI 1a, this pathway is prohibited thermodynamically by more than 1 eV based on density functional theory (DFT) calculations.[14] Further, the new species formed from BPI 7a in the presence of hydroxide shows strong and well-defined NMR signals, confirming that it is diamagnetic and that thermally-induced SET does not occur.

Two alternative interactions between π-acids and anions have been proposed in the literature, namely the formation of a charge-transfer anion-7c complex and the formation of a Meisenheimer complex (FIG. 5A).[13,15] To characterize the reaction of 7a with hydroxide, we performed a UV-visible spectroscopic titration in which mixtures containing increasing molar ratios (i.e. 0:1-100:1) of hydroxide relative to BPI 7a were analyzed (FIG. 5A). The absorption signals corresponding to the unreacted 7a decrease in intensity as the hydroxide concentration increases, in conjunction with the rise of several new signals at λ=~320 and 412 nm.

Monitoring the fluorescence of BPI 7 in these same mixtures (FIG. 5A, inset) shows quenching of the unreacted BPI 7 emission signal along with the appearance of an emission from a new species, supporting assignment of a 1:1 equilibrium binding model. Fitting the UV-vis data to this 1:1 model yields an equilibrium constant for hydroxide association, $K_a$=920 $M^{-1}$ (See SI, section X for details). Further, the UV-vis signals assigned to the complexed form are consistent with Meisenheimer complex formation in that they are blue-shifted rather than red-shifted as has been observed in the formation of a charge-transfer complex between iodide and a NDI.[16] $^{13}C$ NMR data also strongly supports Meisenheimer complex formation. When a solution of BPI 7 is titrated with hydroxide, a new signal is observed in the (FIG. 5B) that we assign as the quaternary carbon that is formed after nucleophilic attack on the imide moiety by hydroxide.

With the dark speciation of BPI 7 defined, the reactivity of the Meisenheimer complex 7b under irradiation was investigated. Given that NDIs have been observed to undergo PET upon light irradiation to form the corresponding NDI radical anions,[17] the irradiation of 7b was investigated to determine if it would lead to similar reactivity. To investigate this possibility, UV-vis was performed on the complex after irradiation in the same 405 nm LED setup used for reactions. After optimizing the irradiation timing through in situ measurements, it was found that a new species forms which reaches maximum concentration after 1 minute, changing the mixture from pale yellow to purple in color with prominent absorption bands at λ=575, ~670, and ~730 nm (FIG. 5D).

Notably, under bulk electrolysis at a potential of $E_{app}$=—2.6 V vs. $Ag/AgNO_3$, the same species is formed after 7 minutes (FIG. 5D). Cyclic voltammetry experiments revealed that 7b undergoes a quasi-reversible reduction at −1.93 V vs. $Ag/AgNO_3$, forming the radical dianion which collapses to radical anion 7c upon homolytic cleavage of hydroxide. Alternatively, we note that the radical dianion of 7b could also serve as the primary reductant when photoexcited. In support of assignment of the signals in FIG. 5C to 7c, we found that the same spectrum is observed when fluoride is used instead of hydroxide, while the radical dianion of 7b formed with fluoride rather than hydroxide would show a distinct spectrum.

Finally, the irradiation step in which radical anion 7c is photoexcited to form the primary reductant 7d was probed via time-resolved absorption spectroscopy. Selective excitation of 7c can be achieved with $\lambda_{pump}$=532 nm, since 7a and 7b have low extinction coefficients at this wavelength. Under these conditions, a relatively long-lived signal was found that upon fitting revealed an excited state lifetime of $\tau$=13 ns (FIG. 5D, right). This signal can be assigned to excited state 7d on the basis of its ground state bleach feature with $\lambda_{max}$=580 nm matching the absorption bands of 7c (FIG. 5D, left). In the presence of benzene, this excited state is quenched significantly, reducing its lifetime to $\tau$=6 ns. In addition, this signal does not return to baseline, indicating the presence of a process that does not reform 7c. In the presence of benzene, this observation is more pronounced, most likely due to direct quenching via PET. Further, control experiments show that 7a in the absence of hydroxide is not quenched by either benzene or the alcohols present in the reaction mixture, suggesting that the species investigated above are responsible for reactivity.

REFERENCES (1) Peters, B. K.; Rodriguez, K. X.; Reisberg, S. H.; Beil, S. B.; Hickey, D. P.; Kawamata, Y.; Collins, M.; Starr, J.; Chen, L.; Udyavara, S.; Klunder, K.; Gorey, T. J.; Anderson, S. L.; Neurock, M.; Minteer, S. D.; Baran, P. S. Scalable and safe synthetic organic electroreduction inspired by Li-ion battery chemistry. *Science* 2019, 363, 838-845.

(2) Chatterjee, A.; Konig, B. Birch-Type Photoreduction of Arenes and Heteroarenes by Sensitized Electron Transfer. *Angew Chem Int Ed Engl* 2019, 0.

(3) Ghosh, I.; Ghosh, T.; Bardagi, J. I.; König, B. Reduction of aryl halides by consecutive visible light-induced electron transfer processes. *Science* 2014, 346, 725-728.

(4) Gosztola, D.; Niemczyk, M. P.; Svec, W.; Lukas, A. S.; Wasielewski, M. R. Excited Doublet States of Electrochemically Generated Aromatic Imide and Diimide Radical Anions. *The Journal of Physical Chemistry A* 2000, 104, 6545-6551.

(5) Gerber, L. C. H.; Frischmann, P. D.; Fan, F. Y.; Doris, S. E.; Qu, X.; Scheuermann, A. M.; Persson, K.; Chiang, Y.-M.; Helms, B. A. Three-Dimensional Growth of Li2S in Lithium-Sulfur Batteries Promoted by a Redox Mediator. *Nano Letters* 2016, 16, 549-554.

(6) Birch, A. J. 117. Reduction by dissolving metals. Part I. *Journal of the Chemical Society* (*Resumed*) 1944, 430-436.

(7) Krapcho, A. P.; Bothner, A. A. Kinetics of the Metal-Ammonia-Alcohol Reductions of Benzene and Substituted Benzenesl. *Journal of the American Chemical Society* 1959, 81, 3658-3666.

(8) Clar, E.; Zander, M. 927. Syntheses of coronene and 1:2-7:8-dibenzocoronene. *Journal of the Chemical Society* (*Resumed*) 1957, 4616-4619.

(9) Manning, S. J.; Bogen, W.; Kelly, L. A. Synthesis, Characterization, and Photophysical Study of Fluorescent N-substituted Benzo[ghi]perylene “Swallow Tail” Monoimides. *The Journal of Organic Chemistry* 2011, 76, 6007-6013.

(10) Clar, E. Polynuclear aromatic hydrocarbons and their derivatives. XIV. Constitution of perylene; syntheses of 2,3,10,11-dibenzo- and of 1,12-benzoperylene, and considerations on the constitution of benzanthrone and phenanthrene. *Ber. Dtsch. Chem. Ges. B* 1932, 65B, 846.

(11) Kennedy, N.; Lu, G.; Liu, P.; Cohen, T. Reductive Lithiation in the Absence of Aromatic Electron Carriers. A Steric Effect Manifested on the Surface of Lithium Metal Leads to a Difference in Relative Reactivity Depending on Whether the Aromatic Electron Carrier Is Present or Absent. *The Journal of Organic Chemistry* 2015, 80, 8571-8582.

(12) Goodson, F. S.; Panda, D. K.; Ray, S.; Mitra, A.; Guha, S.; Saha, S. Tunable electronic interactions between anions and perylenediimide. *Organic & Biomolecular Chemistry* 2013, 11, 4797-4803.

(13) Saha, S. Anion-Induced Electron Transfer. *Accounts of Chemical Research* 2018, 51, 2225-2236.

(14) Aragay, G.; Frontera, A.; Lloveras, V.; Vidal-Gancedo, J.; Ballester, P. Different Nature of the Interactions between Anions and HAT(CN)6: From Reversible Anion-π Complexes to Irreversible Electron-Transfer Processes (HAT(CN)6=1,4,5,8,9,12-Hexaazatriphenylene). *Journal of the American Chemical Society* 2013, 135, 2620-2627.

(15) Dawson, R. E.; Hennig, A.; Weimann, D. P.; Emery, D.; Ravikumar, V.; Montenegro, J.; Takeuchi, T.; Gabutti, S.; Mayor, M.; Mareda, J.; Schalley, C. A.; Matile, S. Experimental evidence for the functional relevance of anion-π interactions. *Nature Chemistry* 2010, 2, 533-538.

(16) Guha, S.; Goodson, F. S.; Corson, L. J.; Saha, S. Boundaries of Anion/Naphthalenediimide Interactions: From Anion-π Interactions to Anion-Induced Charge-Transfer and Electron-Transfer Phenomena. *Journal of the American Chemical Society* 2012, 134, 13679-13691.

(17) Guha, S.; Goodson, F. S.; Roy, S.; Corson, L. J.; Gravenmier, C. A.; Saha, S. Electronically Regulated Thermally and Light-Gated Electron Transfer from Anions to Naphthalenediimides. *Journal of the American Chemical Society* 2011, 133, 15256-15259.

(18) Narayanam, J. M. R.; Stephenson, C. R. J. Visible Light Photoredox Catalysis: Applications in Organic Synthesis. Chem. Soc. Rev. 2011, 40, 102-113.

(19) Prier, C. K.; Rankic, D. A.; MacMillan, D. W. C. Visible Light Photoredox Catalysis with Transition Metal Complexes: Applications in Organic Synthesis. Chem. Rev. 2013, 113, 5322-5363.

(20) Schultz, D. M.; Yoon, T. P. Solar Synthesis: Prospects in Visible Light Photocatalysis. Science 2014, 343, 1239176.

(21) Romero, N. A.; Nicewicz, D. A. Organic Photoredox Catalysis. Chem. Rev. 2016, 116, 10075-10166.

(22) Mortensen, J.; Heinze, J. The Electrochemical Reduction of Benzene-First Direct Determination of the Reduction Potential. Angew. Chem., Int. Ed. Engl. 1984, 23, 84-85.

(23) Ishikawa, H.; Noyes, W. A. The Triplet State of Benzene. J. Am. Chem. Soc. 1962, 84, 1502-1503.

(23) Birch, A. J. 117. Reduction by dissolving metals. Part I. J. Chem. Soc. 1944, 430-436.

(25) Birch, A. J. The Birch Reduction in Organic Synthesis. Pure Appl. Chem. 1996, 68, 553-556.

(26) Lei, P.; Ding, Y.; Zhang, X.; Adijiang, A.; Li, H.; Ling, Y.; An, J. A Practical and Chemoselective Ammonia-Free Birch Reduction. Org. Lett. 2018, 20, 3439-3442.

(27) Birch, A. J. Nature 1946, 158, 60-60.

(28) Peters, B. K.; Rodriguez, K. X.; Reisberg, S. H.; Beil, S. B.; Hickey, D. P.; Kawamata, Y.; Collins, M.; Starr, J.; Chen, L.; Udyavara, S.; Klunder, K.; Gorey, T. J.; Anderson, S. L.; Neurock, M.; Minteer, S. D.; Baran, P. S. Scalable and safe synthetic organic electroreduction inspired by Li-ion battery chemistry. Science 2019, 363, 838-845.

(29) Yasuda, M.; Pac, C.; Sakurai, H. Photochemical reactions of aromatic compounds. 35. Photo-Birch reduction of arenes with sodium borohydride in the presence of dicyanobenzene. J. Org. Chem. 1981, 46, 788-792.

All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

What is claimed:

1. A photoredox catalyst comprising Formula (I) or a salt thereof:

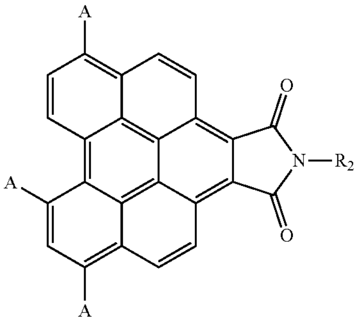

wherein:

A is selected from an optionally substituted $C_1$ to $C_{16}$ alkyl, an optionally substituted aryl, an optionally substituted heteroaryl, a halogen, —CN, —$OR_3$, —C(O)$R_3$, —C(O)$OR_3$, —C(O)$NR_4R_5$, —$NO_2$, —$NR_4R_5$, —$SR_3$, —S(O)$R_3$, —$S(O)_2R_3$, $C_1$ to $C_8$ substituted alkyl, $C_1$ to $C_8$ unsubstituted alkyl;

$R_3$ is selected from —H, —$NR_4R_5$, $C_1$ to $C_8$ substituted alkyl, or $C_1$ to $C_8$ unsubstituted alkyl, substituted aryl, unsubstituted aryl, substituted heteroaryl, or unsubstituted heteroaryl; and $R_4$ and $R_5$ are each independently selected from —H, $C_1$ to $C_8$ substituted alkyl, $C_1$ to $C_8$ unsubstituted alkyl, substituted aryl, unsubstituted aryl, substituted heteroaryl, or unsubstituted heteroaryl; and $R_2$ is selected from an optionally substituted $C_1$ to $C_{16}$ alkyl, an optionally substituted aryl, or an optionally substituted heteroaryl.

2. The photoredox catalyst of claim 1, wherein A is selected from:

A = ;

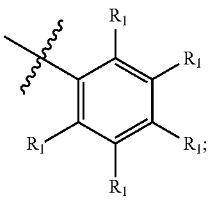

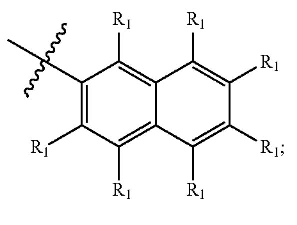

or

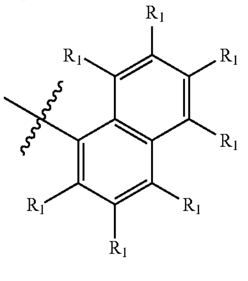

wherein:

$R_1$ is selected from —H, halogen, —CN, —$OR_3$, —C(O)$R_3$, —C(O) $OR_3$, —C(O) $NR_4R_5$, —$NO_2$, -$NR_4R_5$, —$SR_3$, —S(O)$R_3$, —S(O) $2R_3$, $C_1$ to $C_8$ substituted alkyl, $C_1$ to $C_8$ unsubstituted alkyl, substituted aryl, unsubstituted aryl, substituted heteroaryl, or unsubstituted heteroaryl;

$R_3$ is selected from —H, —$NR_4R_5$, $C_1$ to $C_8$ substituted alkyl, or $C_1$ to $C_8$ unsubstituted alkyl, substituted aryl, unsubstituted aryl, substituted heteroaryl, or unsubstituted heteroaryl; and $R_4$ and $R_5$ are each independently selected from —H, $C_1$ to $C_8$ substituted alkyl, $C_1$ to $C_8$ unsubstituted alkyl, substituted aryl, unsubstituted aryl, substituted heteroaryl, or unsubstituted heteroaryl.

3. The photoredox catalyst of claim 2, wherein:

$R_1$ is selected from —H, $C_1$-$C_6$ alkyl, $C_1$-$C_6$ haloalkyl, optionally substituted phenyl, —OH, —O($C_1$-$C_6$ alkyl), —$NO_2$, —CN, —C(═O)OH, —C(═O)O($C_1$-$C_6$ alkyl), —C(═O)O-phenyl, —C(═O)($C_1$-$C_6$ alkyl), —C(═O)-phenyl, —$S(O)_2NH_2$, —$S(O)_2NH$($C_1$-$C_6$ alkyl), —$S(O)_2N$($C_1$-$C_6$ alkyl)($C_1$-$C_6$ alkyl), —S($C_1$-$C_6$ alkyl), —S(O)($C_1$-$C_6$ alkyl), —$S(O)_2$($C_1$-$C_6$ alkyl), —S(phenyl), —S(O)(phenyl), and —$S(O)_2$(phenyl).

4. The photoredox catalyst of claim 2, wherein:

$R_1$ is selected from —H, halogen, —CN, —$OR_3$, —$NR_4R_5$, $C_1$ to $C_8$ substituted alkyl, $C_1$ to $C_8$ unsubstituted alkyl, substituted aryl, unsubstituted aryl, substituted heteroaryl, or unsubstituted heteroaryl;

$R_2$ is selected from $C_1$ to $C_{16}$ substituted or unsubstituted alkyl;

$R_3$ is selected from —H, $C_1$ to $C_8$ substituted alkyl, or $C_1$ to $C_8$ unsubstituted alkyl; and $R_4$ and $R_5$ are independently selected from —H, $C_1$ to $C_8$ substituted alkyl, or $C_1$ to $C_8$ unsubstituted alkyl.

5. The photoredox catalyst of claim 2, wherein:

$R_1$ is selected from H, halogen, CN, $OR_3$, $NR_4R_5$, $C_1$ to $C_4$ substituted alkyl, $C_1$ to $C_4$ unsubstituted alkyl, substituted aryl, unsubstituted aryl, substituted heteroaryl, or unsubstituted heteroaryl;

$R_2$ is selected from $C_1$ to $C_{12}$ substituted or unsubstituted alkyl;

$R_3$ is selected from H, $C_1$ to $C_4$ substituted alkyl, or $C_1$ to $C_4$ unsubstituted alkyl; and $R_4$ and $R_5$ are independently selected from H, $C_1$ to $C_4$ substituted alkyl, or $C_1$ to $C_4$ unsubstituted alkyl.

6. The photoredox catalyst of claim 2, wherein:

$R_1$ is selected from H, fluoride, chloride, bromide, CN, $OR_3$, $NR_4R_5$, methyl, ethyl, n-propyl, iso-propyl, n-butyl, sec-butyl, iso-butyl, t-butyl, $CCl_3$, $CF_3$, phenyl;

$R_2$ is selected from $C_1$ to $C_8$ substituted or unsubstituted alkyl;

$R_3$ is selected from H, methyl, ethyl, n-propyl, iso-propyl, n-butyl, sec-butyl, iso-butyl, t-butyl; and $R_4$ and $R_5$ are independently selected from H, methyl, ethyl, n-propyl, iso-propyl, n-butyl, sec-butyl, iso-butyl.

7. The photoredox catalyst of claim 2, wherein:

$R_1$ is selected from H, bromide, CN, $OR_3$, $NR_4R_5$, $CF_3$, phenyl; $R_2$ is 2-ethylhexyl; and $R_3$, $R_4$, and $R_5$ are methyl.

* * * * *